(12) United States Patent
Lefenfeld et al.

(10) Patent No.: US 7,211,539 B2
(45) Date of Patent: May 1, 2007

(54) SILICA GEL COMPOSITIONS CONTAINING ALKALI METALS AND ALKALI METAL ALLOYS

(75) Inventors: Michael Lefenfeld, New York, NY (US); James L. Dye, East Lansing, MI (US)

(73) Assignees: SIGNa Chemistry, LLC, New York, NY (US); Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/995,327

(22) Filed: Nov. 24, 2004

(65) Prior Publication Data

US 2005/0151278 A1 Jul. 14, 2005

Related U.S. Application Data

(60) Provisional application No. 60/611,700, filed on Sep. 22, 2004, provisional application No. 60/611,701, filed on Sep. 22, 2004, provisional application No. 60/578,818, filed on Jun. 14, 2004, provisional application No. 60/561,886, filed on Apr. 14, 2004, provisional application No. 60/524,038, filed on Nov. 24, 2003.

(51) Int. Cl.
*B01J 21/00* (2006.01)
*B01J 20/00* (2006.01)
*B01J 23/02* (2006.01)

(52) U.S. Cl. .................. 502/237; 502/233; 502/243; 502/344; 502/407; 502/411; 502/439

(58) Field of Classification Search ............... 502/233, 502/237, 243, 344, 407, 411, 439
See application file for complete search history.

(56) References Cited

U.S. PATENT DOCUMENTS 1,665,264 A * 4/1928 Holmes et al. ............. 423/338

(Continued)

OTHER PUBLICATIONS

R. Qadeer, S. Akhtar, F. Mahmood, "Nitrogen Adsorption On Metal Impregnated Alumina by Continuous Flow Method" Back to Journal of IAS, vol. 8, No. 4, 1995.

(Continued)

*Primary Examiner*—Cam N. Nguyen
(74) *Attorney, Agent, or Firm*—Nixon Peabody, LLP

(57) ABSTRACT

The invention relates to Group 1 metal/silica gel compositions comprising silica gel and an alkali metal or an alkali metal alloy. The compositions of the inventions are described as Stage 0, I, II, and III materials. These materials differ in their preparation and chemical reactivity. Each successive stage may be prepared directly using the methods described below or from an earlier stage material. Stage 0 materials may, for example, be prepared using liquid alloys of Na and K which are rapidly absorbed by silica gel (porous $SiO_2$) under isothermal conditions, preferably at or just above room temperature, to form loose black powders that retain much of the reducing ability of the parent metals. When the low melting Group 1 metals are absorbed into the silica gel, a mild exothermic reaction produces Stage I material, loose black powders that are indefinitely stable in dry air. Subsequent heating to 400° C. produces Stage II materials, which are also loose black powders. Further heating above 400° C. forms Stage III material with release of some Group 1 metal. It is believed that Stage I, II and III materials represent reductions of the silica gel after absorption of the Group 1 metal. Preferred Group 1 metal/silica gel compositions of the invention are those containing sodium, potassium, or sodium-potassium alloys with sodium and sodium-potassium alloys being most preferred. Each stage of the Group 1 metal/silica gel composition of the invention may be used as a reducing agent reacting with a number of reducible organic materials in the same manner known for alkali metals and their alloys.

33 Claims, 9 Drawing Sheets

U.S. PATENT DOCUMENTS

| | | | |
|---|---|---|---|
| 1,939,647 A * | 12/1933 | Arnold et al. ............... 502/180 |
| 2,337,419 A | 12/1943 | Sensel |
| 2,378,290 A * | 6/1945 | Drake et al. ................ 502/236 |
| 2,731,326 A | 1/1956 | Alexander et al. |
| 2,740,820 A | 4/1956 | Wilson et al. |
| 2,765,242 A | 10/1956 | Alexander et al. |
| 2,816,917 A | 12/1957 | Hansley et al. |
| 3,033,800 A * | 5/1962 | Elliott, Jr. et al. .......... 502/254 |
| 3,033,801 A * | 5/1962 | Kloepfer ..................... 502/250 |
| 3,079,234 A | 2/1963 | Jenkins et al. |
| 3,165,379 A | 1/1965 | Schwartz et al. |
| 3,274,277 A | 9/1966 | Bloch et al. |
| 3,290,790 A | 12/1966 | Kunii et al. |
| 3,322,495 A | 5/1967 | Magee |
| 3,347,944 A | 10/1967 | Fritz et al. |
| 3,405,196 A | 10/1968 | Wolff |
| 3,489,516 A | 1/1970 | Kummerle |
| 3,493,341 A | 2/1970 | Le Page et al. |
| 3,507,810 A * | 4/1970 | Lindsley et al. ............ 502/159 |
| 3,527,563 A | 9/1970 | Shanklin |
| 3,535,262 A * | 10/1970 | Nappier et al. ........ 252/186.33 |
| 3,575,885 A * | 4/1971 | Hunter et al. ............... 502/402 |
| 3,576,891 A | 4/1971 | Rosenthal |
| 3,577,473 A | 5/1971 | Nagase et al. |
| 3,658,724 A * | 4/1972 | Stiles ......................... 502/183 |
| 3,670,033 A | 6/1972 | Izawa et al. |
| 3,679,605 A | 7/1972 | Sanford et al. |
| 3,793,382 A | 2/1974 | Higuchi et al. |
| 3,794,712 A * | 2/1974 | Aboutboul et al. ......... 423/338 |
| 3,801,705 A * | 4/1974 | Krekeler et al. ............ 423/338 |
| 3,808,152 A | 4/1974 | Nagase et al. |
| 3,878,289 A | 4/1975 | Beavon |
| 3,897,509 A | 7/1975 | Nagase et al. |
| 3,915,995 A | 10/1975 | Holmes et al. |
| 3,928,485 A | 12/1975 | Nagase et al. |
| 3,954,896 A | 5/1976 | Shima et al. |
| 4,087,477 A | 5/1978 | Tazuma et al. |
| 4,168,247 A | 9/1979 | Hayden et al. |
| 4,205,192 A | 5/1980 | Harada |
| 4,229,610 A | 10/1980 | Myers et al. |
| 4,248,741 A | 2/1981 | Wernli et al. |
| 4,276,279 A | 6/1981 | Robinson et al. |
| 4,313,925 A | 2/1982 | Bamberger |
| 4,353,815 A | 10/1982 | Antos |
| 4,366,091 A | 12/1982 | Antos |
| 4,394,302 A | 7/1983 | Miller et al. |
| 4,413,156 A | 11/1983 | Watts, Jr. et al. |
| 4,435,606 A | 3/1984 | Motz et al. |
| 4,440,631 A | 4/1984 | Togari et al. |
| 4,446,251 A | 5/1984 | Bartley et al. |
| 4,471,075 A | 9/1984 | Bartley et al. |
| 4,508,930 A | 4/1985 | Wideman et al. |
| 4,633,029 A | 12/1986 | Tillett, Jr. et al. |
| 4,675,307 A | 6/1987 | Taniguchi et al. |
| 4,720,601 A | 1/1988 | Suzukamo et al. |
| 4,727,204 A | 2/1988 | Suzukamo et al. |
| 4,769,501 A | 9/1988 | Iwahara |
| 4,837,194 A | 6/1989 | Hayden |
| 4,975,405 A | 12/1990 | Okamura et al. |
| 4,982,044 A | 1/1991 | Smith |
| 5,008,480 A | 4/1991 | Slaugh |
| 5,128,291 A | 7/1992 | Wax et al. |
| 5,292,985 A | 3/1994 | Lattner et al. |
| 5,856,262 A | 1/1999 | Flick et al. |
| 6,022,823 A | 2/2000 | Augustine et al. |
| 6,096,934 A | 8/2000 | Rekoske |
| 6,399,538 B1 | 6/2002 | Hucul |
| 6,403,852 B1 | 6/2002 | Yamamoto et al. |
| 6,492,014 B1 * | 12/2002 | Rolison et al. ............ 428/317.9 |
| 6,548,711 B2 | 4/2003 | Yamamoto et al. |
| 6,586,636 B2 | 7/2003 | Kelly |
| 6,706,928 B2 | 3/2004 | Kelly |

OTHER PUBLICATIONS

L. F. Fieser, M. Fieser, "Topics in Organic Chemistry". (Reinhold, New York, 1963) pp. 514-515.

A. Wurtz, "Ueber eince neue Klasse organischer Radicale; nach" Justus Liebig Ann. Chem. 96, 364-375 (1855).

P. P. Edwards, P. A. Anderson, J. M. Thomas, "Dissolved Alkali Metals in Zeolites" Accounts of Chemical Research 29, 23-29 (1996).

J. A. Rabo, P. H. Angell, P. H. Kasai, V. Schomaker, Studies of Cations in Zeolites: Adsorption of Carbon Monoxide; Formation of Ni ions and Na$_{\frac{3}{4}}^{+}$ centres, Discussions of the Faraday Society 41, 328-349 (1966).

P. A. Anderson, D. Barr, P. P. Edwards, "Solvated Electrons in the Synthesis of Ionic Clusters in Zeolites**" Angewandte Chemie International Edition in English 11, 1501-1502 (1991).

K.M. Unruh, T.E. Huber, and C.A. Huber, "Melting and freezing behavior of indium metal in porous glasses," Physical Review B, Sep. 15, 1993, pp. 9021-9027, vol. 48, No. 12, The American Physical Society.

J. Monte Russell, Michal Sabat, and Russell N. Grimes, "Organotransition-Metal Metallacarboranes. 59. Synthesis and Linkage of Boron-Functionalized Ferracarborane Clusters," Organometallics, 2002, 21, pp. 4113-4128, American Chemical Society.

Jaacov Levy, Dov Tamarkin, Henry Selig, and Mordecai Rabinovitz, "Potassium Metal Dispersed on Silica: A Versatile Reagent in Organic Chemistry," Angew. Chem. Int. Ed. Engl. 20, 1981, No. 12, p. 1033, Verlag Chemie GmbH, 6940 Weinheim.

Tetsuya Kodaira, Yasuo Nozue, Satoshi Ohwashi, Takenari Goto, and Osamu Terasaki, "Optical Properties of Potassium Clusters Incorporated into Zeolite LTA," Physical Review B, Oct. 15, 1993, pp. 12245-12252, vol. 48, No. 16, The American Physical Society.

V.I. Srdanov, G.D. Stucky, E. Lippmaa, and G. Engelhardt, "Evidence for an Antiferromagnetic Transition in a Zeolite-Supported Cubic Lattice of $F$ Centers," Physical Review Letters, Mar. 16, 1998, pp. 2449-2452, vol. 80, No. 11, The American Physical Society.

Yasuo Nozue, Tetsuya Kodaira, Satoshi Ohwashi, Takenari Goto, and Osamu Terasaki, "Ferromagnetic Properties of Potassium Clusters Incorporated into Zeolite LTA," Physical Review B, Oct. 15, 1993, pp. 12253-12261, vol. 48, No. 16, The American Physical Society.

Andrew S. Ichimura, James L. Dye, Miguel A. Camblor, and Luis A. Villaescusa, "Toward Inorganic Electrides," J. Am. Chem. Soc., 2002, pp. 1170-1171, vol. 124, No. 7, American Chemical Society.

Daryl P. Wernette, Andrew S. Ichimura, Stephanie A. Urbin, and James L. Dye, "Inorganic Electrides Formed by Alkali Metal Addition to Pure Silica Zeolites," Chem. Mater., 2003, pp. 1441-1448, vol. 15, No. 7, American Chemical Society.

V. Petkov, S.J.L. Billinge, T. Vogt, A.S. Ichimura, and J.L. Dye, "Structure of Intercalated Cs in Zeolite ITQ-4: An Array of Metal Ions and Correlated Electrons Confined in a Pseudo-1D Nanoporous Host," Physical Review Letters, Aug. 12, 2002, pp. 075502-1-075502-4, vol. 89, No. 7, The American Physical Society.

Jiliang He, Dennis D. Klug, Kentaro Uehara, Keith F. Preston, Christopher I. Ratcliffe, and John S. Tse, "NMR and X-ray Spectroscopy of Sodium—Silicon Clathrates," J. Phys. Chem. B, 2001, pp. 3475-3485, vol. 105, No. 17, American Chemical Society.

420875 LUDOX® AM-30 colloidial silica, Aldrich, 30 wt. % suspension in H2O). http://www.sigmaaldrich.com/catalog/search/ProductDetail/ALDRI....

236845 Silica gel , Sigma-Aldrich Davisil®, ≧99%, Grade 646, 35-60 mesh., http://www.sigmaaldrich.com/catalog/search/ProductDetail/SIAL/2....

International Search Report dated Mar. 15, 2006.
International Search Report dated Jan. 6, 2006.

* cited by examiner

A. GC Trace

B. Mass Spectrum

C. $^1$H NMR

1

SILICA GEL COMPOSITIONS CONTAINING ALKALI METALS AND ALKALI METAL ALLOYS

RELATED APPLICATION DATA

This application claims benefit of priority of Provisional Application Ser. Nos. 60/524,038 filed Nov. 24, 2003; 60/561,886 filed on Apr. 14, 2004; 60/578,818 filed on Jun. 14, 2004; 60/611,701 filed on Sep. 22, 2004; and 60/611,700 filed on Sep. 22, 2004; the entire disclosures of which are incorporated herein by reference.

FIELD OF THE INVENTION

The invention relates to silica gel compositions made by interaction of alkali metals or alloys of these metals with silica gel. The compositions have improved handling characteristics and retain the reactivity of the neutral alkali metal or alloy.

BACKGROUND OF THE INVENTION

Alkali metals, those in Group 1 of the periodic table, and alloys of alkali metals, are very reactive in their metallic, or neutral, state. The alkali metals and their alloys are very reactive toward air and moisture and may catch fire spontaneously when exposed to these agents. To avoid the inherent hazards associated with their activity, the neutral metal or alloy must often be stored in vacuo or under an inert liquid such as oil in order to protect it from contact with the atmosphere, which may result in oxidation or other reactions. For example, sodium metal is often stored in Nujol oil which must, to avoid unwanted impurities, be removed prior to use in chemical reactions. This places severe restrictions on its shipment and use.

The combination of alkali metals with silica zeolites, such as ZSM-5, has been extensively studied in many laboratories. For example, it was recently shown that pure silica zeolites can absorb up to 12 mole percent cesium from the vapor phase and comparable amounts of the other alkali metals (except lithium). Prior research with alkali metal encapsulation in all-silica zeolites revealed that such a combination reacts exothermically with water to produce hydrogen quantitatively. (See, for example, "Toward Inorganic Electrides", A. S. Ichimura, J. L. Dye, M. A. Camblor and L. A. Villaescusa, *J. Am. Chem. Soc.*, 124, 1170–1171 (2002) and "Inorganic Electrides Formed by Alkali Metal Addition to Pure Silica Zeolites", D. P. Wernette, A. S. Ichimura, S. A. Urbin and J. L. Dye, *Chem. Mater.* 15, 1441–1448, (2003). The concentration of sodium absorbed by the zeolite compositions, however, was too low to be practical. In addition, the reaction was relatively slow with slow sodium diffusion within the limited zeolite pore size.

The use of potassium metal dispersed on silica as a reagent in organic synthesis has been reported by Levy et al., *Angew. Chem. Int. Ed. Engl.* 20 (1981) p. 1033. Potassium metal was dispersed onto silica gel (CAS Registry No. 7631-86-9: actually colloidal silica, which has no internal surface area) producing an amorphous material. The reactivity of the material was demonstrated with water and benzophenone, as shown below. See also, Russel, et al., Organometallics 2002, 21, 4113–4128, Scheme 3.

A need exists, therefore, to have alkali metals and their alloys available in a form that may be easily handled without a significant loss in metal reactivity. This invention answers that need.

SUMMARY OF THE INVENTION

The invention relates to a Group 1 metal/silica gel composition comprising the product of mixing a liquid Group 1 metal with silica gel in an inert atmosphere under isothermal conditions sufficient to absorb the liquid Group 1 metal into the silica gel pores. The Group 1 metal/silica gel composition produced reacts with dry $O_2$. This material is referred to as "Stage 0" material.

The invention also relates to a Group 1 metal/silica gel composition comprising the product of mixing a liquid Group 1 metal with silica gel under exothermic conditions sufficient to absorb the liquid Group 1 metal into the silica gel pores. The Group 1 metal/silica gel composition produced does not react with dry $O_2$. This material is referred to as "Stage I" material.

In addition, the invention relates to a Group 1 metal/silica gel composition comprising the product of mixing a liquid Group 1 metal with silica gel under conditions sufficient to absorb the liquid Group 1 metal into the silica gel pores and heating the resulting mixture to a temperature of between about 215° C. to about 400° C. The Group 1 metal/silica gel composition produced does not react with dry $O_2$. This material is referred to as "Stage II" material.

The invention also relates to a Group 1 metal/silica gel composition comprising the product of mixing a liquid Group 1 metal with silica gel under conditions sufficient to absorb the liquid Group 1 metal into the silica gel pores and heating the resulting mixture to a temperature of above about 400° C. The Group 1 metal/silica gel composition produced does not react with dry $O_2$. This material is referred to as "Stage III" material.

DETAILED DESCRIPTION OF THE INVENTION

Figure 1:
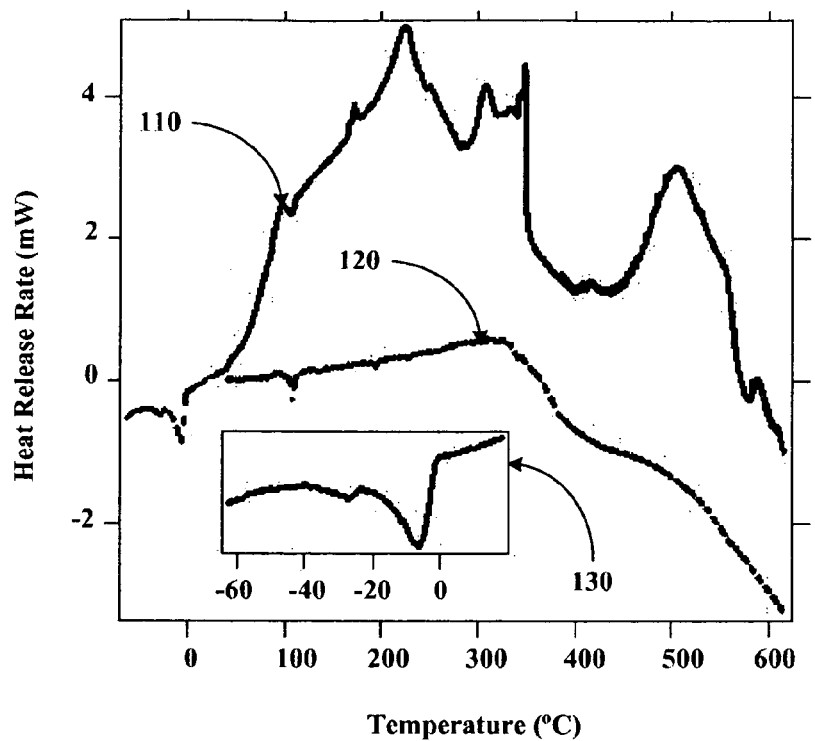
FIG. 1 is a Differential Scanning Calorimetry (DSC) diagram showing traces of a 1:1 NaK/silica gel sample (8.9 mg).

Group 1 Metals: Alkali Metals and Alkali Metal Alloys

Alkali metals are those metals in the Group 1 family of the periodic table. The terms "Group 1 metal" or "Group 1 metals" are used here to describe alkali metals and alloys of alkali metals which may be used in the silica gel compositions of the invention. Those alkali metals include sodium (Na), potassium (K), rubidium (Rb), and cesium, (Cs). Of these alkali metals, sodium and potassium are preferred for use in the silica gel compositions of the invention, with sodium being particularly preferred.

Alkali metal alloys may also be used in the silica gel compositions of the invention. The alkali metal alloy is preferably an alloy of two or more alkali metals, for example sodium-potassium (NaK) alloys, which are particularly preferred. Other preferred alkali metal alloys are those containing, potassium, cesium, and rubidium with each other and particularly alloys of these elements with sodium. The alkali metal alloys are within the "Group 1 metal" definition as used in the specification and claims.

In preparing the Group 1 metal/silica gel compositions of the invention, the Group 1 metal is typically mixed with the silica gel. The viscosity of the liquid Group 1 metal should be at least low enough to be absorbed by the silica gel. One method to accomplish this is heating the alkali metal in an inert atmosphere prior to mixing it with the silica gel. Alternatively, depending on the stage of material to be prepared, the Group 1 metal may be mixed as a solid with the silica gel and the mixture heated to melt the alkali metal.

Another method to introduce Group 1 metals into silica gel is from the vapor phase as was done with zeolites. (See A. S. Ichimura, J. L. Dye, M. A. Camblor and L. A. Villaescusa, *J. Am. Chem. Soc.*, 124, 1170–1171 (2002) and D. P. Wernette, A. S. Ichimura, S. A. Urbin and J. L. Dye, *Chem. Mater.* 15, 1441–1448, (2003).) In another method, a Group 1 metal can be deposited onto the silica gel from a metal-ammonia solution. (See M. Makesya and K. Grala, Syn. Lett. 1997, pp. 267–268, "Convenient Preparation of 'High Surface Sodium' in Liquid Ammonia: Use in Acyloin Reaction.") The metal-ammonia solution can be used to avoid agglomeration of the metal in upon mixing with the silica gel and to prepare an intimate mixture of the metal with the silica gel. However, in practice the metal-ammonia solution method of mixing Group 1 metals with silica gel was accompanied by considerable decomposition of the metal-ammonia solution to form amides. However, as preferred for the invention, simply allowing the liquid Group 1 metal to contact the silica gel avoids the time-consuming vapor deposition or metal-ammonia routes.

As discussed below, for at least Stage 0 material, it is generally preferred that the Group 1 metal have a melting point within about 15° C. of room temperature (25° C.). For example cesium and rubidium have melting points of 28.5° C. and 38.5° C., respectively. Typically alloys of the two or more alkali metals are, and preferably are, liquid at or near room temperature. A preferred low-melting alloy is that between sodium and potassium (NaK) at various molar ratios of Na to K between 0.5 and 3.0 more preferably with a 2:1 molar ratio, $Na_2K$. All Na—K alloys with mole ratios between 0.5 and 2.5 begin melting eutectic melting temperature of −12.6° C. Melting is complete at 25° C. for mole ratios of about 0.12 and 3.1. Other binary alloys of the alkali metals, such as Cs with Rb, K, or Na and Rb with Na or K also melt below, or only slightly above room temperature and would therefore be appropriate to use for this purpose. Ternary alloys, made from three of these four alkali metals, or an alloy of all four would also melt at low enough temperatures to form a Group 1 metal/silica gel composition of the invention.

Silica Gel

Silica gel is a porous form of amorphous silica. It is a free-flowing powder that is listed as 99+ percent $SiO_2$. Silica gel is readily available and inexpensive. Silica gel generally has a pore volume ranging from about 0.6 to about 1.2 $cm^3/g$, and a surface area ranging from about 300 to about 750 $m^2/g$. Silica gel is commonly available in the following mesh sizes: 3–8, 6–16, 14–20, 14–42, 30–60, 28–200, and as small as mesh 325. Given its porous nature, silica gel can take up large amounts of absorbed material. The silica gels used in the silica gel compositions of the invention preferably have pore sizes ranging from 50 Å to 1000 Å. Preferably, the pore size may range from 100 to 300 Å. More preferably, the average diameter of the pores of the silica gel will be approximately 150 Å. Preferred forms of silica gel include Davisil™ Grades 646 and 50, which are both 30 to 60 mesh obtained from chemical suppliers such as Aldrich and directly from the Davison Chemical Division of WR Grace Company, (i.e., 150 Å pore size, granular, 30–60 mesh, plain white, no indicator). An alternate supplier of such silica gel is the Eagle Chemical Division of Multisorb.

Although silica gel, when purchased, is a free-flowing powder, it typically contains large amounts of gaseous material, such as water and air. These are preferably removed prior to mixing the silica gel with an alkali metal or alloy to form compositions of the invention. The silica gel may be degassed using methods known in the art. For example, to remove the gaseous material the silica gel may be heated under vacuum in an evacuable flask, first with a hot air dryer and then with a torch. Such heating achieves temperatures of approximately 300° C. It is also possible, and is actually preferred, to remove the gases more easily and to passivate active sites by heating the silica gel to 600° C. or hotter (900° C.) in air (calcination). It is believed that heating the silica gel to 600° C. or higher causes at least some of Si—OH sites in the pores or silica gel lattice to form siloxane, Si—O—Si, groups with the concomitant loss of water. Heating the silica gel at a lower temperature would also produce a usable starting material, but a portion of the alkali metal would probably be rendered inert by reaction with defect Si—OH groups. The silica gel is typically cooled to room temperature before preparing a Group 1 metal/silica gel composition of the invention.

Silica Gel Compositions Containing Alkali Metal and Alkali Metal Alloys

The ability to utilize alkali metals or their equivalents in a convenient form continues to be a need in the chemical industry and for the hydrogen production community. Answering that need, the invention relates to Group 1 metal/silica gel compositions comprising silica gel and an alkali metal or an alkali metal alloy. The compositions of the inventions are described as Stage 0, I, II, and III materials. These materials differ in their preparation and chemical reactivity. Each successive stage may be prepared directly using the methods described below or from an earlier stage material. Stage 0 materials may, for example, be prepared using liquid alloys of Na and K which are rapidly absorbed by silica gel (porous $SiO_2$) under isothermal conditions, preferably at or just above room temperature, to form loose black powders that retain much of the reducing ability of the parent metals. It is believed the Stage 0 materials have small clusters of neutral Group 1 metal absorbed in the siica gel pores. The Stage 0 materials are pyrophoric but less explosive in air as compared to their parent Group 1 metal. Stage I materials may be prepared by heating Stage 0 materials at 140° C. overnight. Stage I material is a loose black powder that are indefinitely stable in dry air. Subsequent heating to 400° C. produces Stage II materials, which are also loose black powders. Further heating above 400° C. forms Stage III material with release of some Group 1 metal. It is believed that Stage I, II and III materials represent reductions of the silica gel after absorption of the Group 1 metal. Preferred Group 1 metal/silica gel compositions of the The Group 1 metal/silica gel compositions of the invention react rapidly with water to produce gaseous hydrogen in near quantitative yield, typically about 95% yield. The Group 1 metal/silica gel compositions of the invention, whose preparation and properties are described below, show promise as easily shipped and handled sources of clean hydrogen and as powerful reducing agents for a variety of reactions of organic compounds. Table I below summarizes the preparation processes and uses of Stage 0, I, II, and III materials.

TABLE I

Summary of Stages 0, I, II, and III

| Material Type | Preferred Metals/Alloys Used | Preparation Procedures |
| --- | --- | --- |
| Stage 0 | Liquid alloys (NaK, Na$_2$K, etc.) | Under inert atmosphere or vacuum, liquid alkali metal alloy is added to silica gel at or near room temperature. On a large-scale, this process would be best done by adding the liquid metal or alloy to silica gel spread in a metal pan that would dissipate any heat which may be produced. |
| Stage I | Liquid alloys (NaK, Na$_2$K, etc.) Cesium, Rubidium, etc. | Under inert atmosphere or vacuum, liquid or vapor alkali metal is added to silica gel and is agitated for several minutes to hours at a temperature below 150° C. |
| Stage II | Sodium Potassium Na—K alloys | Under inert atmosphere or vacuum, alkali metal or alloy is added to silica gel and is heated to between 215° C.–400° C. to incorporate all metal and to reduce sensitivity to air. |
| Stage III | Sodium Potassium Na—K alloys | Under inert atmosphere or vacuum, alkali metal or alloy is added to silica gel and is heated to 215° C. to incorporate all metal, and then gradually heated above 400° C. over several hours which makes a Si-rich silicide in the silica gel. | invention are those containing sodium, potassium, or sodium-potassium alloys with sodium and sodium-potassium alloys being most preferred.

As described below, a number of samples of this material with NaK and cesium, at various loads and mass ratios, were tested by Differential Scanning Calorimetry (DSC). The heat absorbed upon melting NaK in the silica gel pores at −25–0° C. was used to determine the amount of encapsulated metal that remained as metal in the silica gel. This was followed by broad exothermic peaks between 5° C. and 650° C. Upon cooling and reheating the same sample, no appreciable thermal peaks were observed. This shows that the heat treatment causes encapsulated metal in the pores to react with silica gel to produce Stage II and then Stage III material, although the boundaries are not sharp. This conversion to Stage II and III material does not appreciably change the hydrogen producing abilities of the material.

The Group 1 metal/silica gel compositions of the invention comprise silica gel with absorbed Group 1 metal. The amount of Group 1 metal loading is dependent upon the pore size and pore density of the actual silica gel used. Typically, the Group 1 metal may be present in the compositions of the invention up to about 50% by weight. Preferably, the amount of metal ranges from 30% to 40% by weight. In the Stage I, II, and III materials of the invention, loadings above about 40% by weight result in some free metal remaining in the silica gel pores.

As discussed above, to prepare all of the Group 1 metal/silica gel compositions of the invention, it is preferred to degas and passivate the silica gel prior to mixing it with the Group 1 metal. Typically, in preparing the materials of the invention, the silica gel is initially heated to approximately 600° C. or higher in air to remove water, de-gas the silica gel, and minimize defect sites. Other methods known in the art to dry, de-gas and/or passivate the silica gel may also be used.

Stage 0 Material

The Stage 0 material of the invention apparently contains low-melting Group 1 metals absorbed into the pores of silica gel without reaction or metal redistribution into the silica gel lattice. Thus, it can be viewed as nanoscale alkali metal or alkali metal alloy particles in the open pores and channels absorbed within the silica gel. The Stage 0 material of the invention is a Group 1 metal/silica gel composition comprising the product of mixing a liquid Group 1 metal or a liquid Group 1 metal alloy, such as Na$_2$K, with silica gel under isothermal conditions sufficient to absorb the liquid Group 1 metal or liquid Group 1 metal alloy into the silica gel pores. Preferred Group 1 metals for Stage 0 materials include a low-melting Group 1 metal such as cesium or a NaK alloy. The Stage 0 Group 1 metal/silica gel composition reacts with dry O$_2$, which differentiates it from Stage I, II, and III materials. Since Stage 0 material is reactive with dry air, it should be handled in vacuo, in an oxygen-free atmosphere, and preferably in an inert atmosphere, such as under nitrogen or an inert gas. While the Stage 0 material will ignite spontaneously in air, it can be stored under such conditions in a closed container, e.g. a screw-top vial.

To form Stage 0 materials, a Group 1 metal is mixed with silica gel in an inert atmosphere under isothermal conditions, preferably at room temperature or slightly above, for a time sufficient to permit the alkali metal or alloy to be absorbed into the silica. The mixing must be done in an inert atmosphere such as within a glove box or glove bag. During formation of a preferred Stage 0 material, a liquid Group 1 metal, such as $Na_2K$, may be poured over a bed of silica gel at room temperature. The mixture is agitated, preferably stirred or shaken, to achieve good mixing. The liquid Group 1 metal is preferably absorbed into the porous silica gel without any significant heat of reaction or appreciable release of heat.

Depending upon the Group 1 metal used, the absorption of the liquid Group 1 metal to form Stage 0 material preferably occurs within 15° C. of room temperature (25° C.). In the typical process, so little heat is evolved that the sample does not become noticeably warm but converts to a product which is a free-flowing amorphous black powder, in which the individual particles have a shiny surface. The mixture is agitated for a time sufficient to allow the alkali metal or alloy to be absorbed or "soaked up" by the silica gel. The time of mixing generally depends upon the batch size of material being prepared and may range from several minutes to several hours. (This mixing time holds true for the preparation of any Group 1 metal/silica gel composition of the invention.)

When preparing Stage 0 material, any heat generated by the reaction or put into the reaction should be controlled or dissipated. A significant temperature increase during the preparation should be avoided. In a preferred embodiment the Stage 0 material is formed near room temperature (25° C.). Heating much above this temperature generally leads to the formation of Stage I material. The temperature may be controlled by spreading the silica gel (for example, on a metal tray), stirring the silica gel, or by cooling the reaction vessel. The reaction temperature should, however, be maintained such that the Group 1 metal remains liquid so that it may be absorbed by the silica gel. It should also be noted that Stage 0 material can slowly convert to Stage I material over time when kept at room temperature, although further conversion to Stage II material does not occur without heating as discussed below.

The Stage 0 material is a shiny black powder that reacts exothermically with water. A DSC of the Stage 0 material shows the presence of the alkali metal in its neutral state within the silica gel. While the exact composition of the Stage 0 material is not currently known, the melting point of the Stage 0 material is lower than the melting point of the most common Group 1 alloys, such as NaK, thus indicating that small particles of the Group 1 alloys are within the pores of the silica gel.

Figure 4:
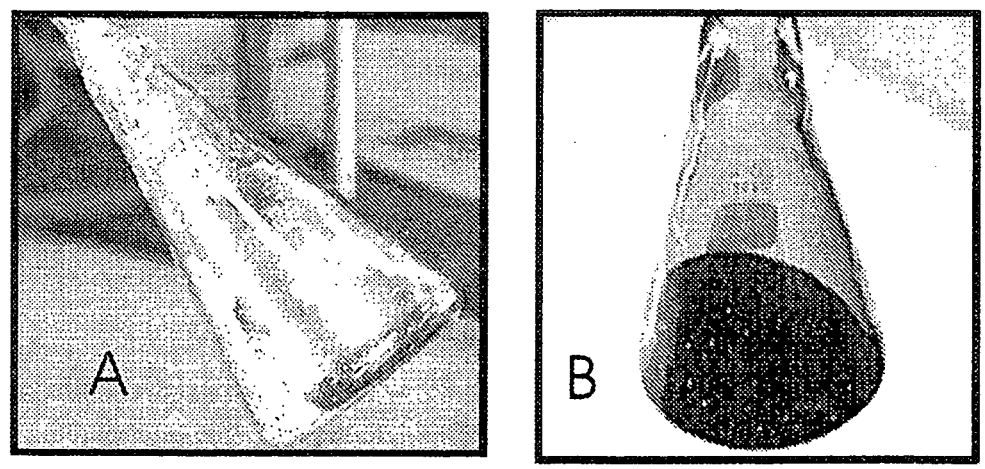
FIG. 4 shows the conversion of silica gel particles coated with an alloy of composition $Na_2K$ to the loose, shiny, black Stage I powder.

FIG. 4 illustrates the absorption of $Na_2K$ alloy into silica gel at room temperature to form a loose, shiny, black Stage 0 powder. As shown in FIG. 4, the flask shown in (A) contains silica gel coated with $Na_2K$ alloy immediately after mixing. The flask shown in (B) contains the final loose black material after shaking the sample in flask (A) for a few minutes. It is an apparently homogeneous, easily poured black powder.

The Stage 0 materials are the most reactive members of the Group 1 metal/silica gel compositions of the invention. Since the addition of a low-melting alkali metal or alloy to silica gel produces a Stage 0 material without significant heat evolution, the Stage 0 material retains most of the reducing ability of the alkali metal. Because of their reactivity toward air and moisture they must be handled with care and not allowed to come in contact with large amounts of air and moisture. In spite of these restrictions, the Stage 0 materials have utility in highly reducing chromatography applications. The porosity of packed columns of the Group 1 metal/silica gel compositions of the invention provide a reducing environment that cannot be met with the parent metals or alloys. This, as discussed below, permits the Stage 0 material to be used to produce hydrogen from water and as a reducing agent reacting with a number of reducible organic materials in a manner similar to that of the pure alkali metals.

Stage I Material

The Stage I material of the invention is a Group 1 metal/silica gel composition comprising the product of mixing a liquid Group 1 metal with silica gel under exothermic conditions sufficient to absorb the liquid Group 1 metal into the silica gel pores. The Stage I Group 1 metal/silica gel composition produced does not react with dry $O_2$. In the Stage I material it appears that the alkali metal or alloy has been converted to a form that loses the properties of the bulk metal, such as melting. The framework within which the active reducing material is dispersed appears to be largely $SiO_2$. Pair Distribution Function experiments on the Stage I material exhibit predominantly silicon and oxygen peaks with no crystallinity which suggests that the alkali metal(s) have ionized to form alkali cations, with the electrons released to the silica framework or to the void spaces. See Billinge, et al., Chem. Commun. 2004, pp. 749–760 for a discussion of Pair Distribution Function.

The Stage I material of the invention may be formed by mixing the liquid Group 1 metal, at or just above its melting point with silica gel under an inert atmosphere to allow the Group 1 metal to be absorbed into the pores of the silica gel. The Group 1 metal may also be mixed with the silica gel using one of the alternative methods discussed above, such as adding the Group 1 metal as a vapor. The mixture is then maintained at or slightly above the melting point of the Group 1 metal (i.e., approximately 70° C. to 150° C.) and agitated for between several minutes to several hours. Generally speaking, higher reaction temperatures convert the material in shorter times. The reaction to form Stage I materials is mildly exothermic, and, on a large scale, the process would be preferably done by adding the liquid metal or alloy to the silica gel in a metal pan that would remove heat as it is produced. The reaction appears to form an alkali metal—silica gel lattice. The exothermic nature of the reaction differentiates Stage I material from Stage 0 material. Heating above the exotherm can convert Stage I material to Stage II or Stage III material, depending upon the temperature.

When low-melting Group 1 metals are added to calcined and outgassed SG in a closed environment such as an Erlenmeyer flask, the system often becomes warm because of exothermic reactions between the alkali metal and the silica gel or its defect sites. This can result in the formation of mixtures of Stages 0 and I. The simplest and most direct preparation of Stage I materials is to heat Stage 0 samples overnight under an inert atmosphere at temperatures of 140° C. Other times and temperatures may work also, but care should be taken to avoid overheating, which can lead to the formation of Stage II. To insure a homogeneous product, provision should be made for agitation during the heating process.

The Stage I material is an amorphous, shiny black powder that does not immediately react with dry air, but reacts exothermically with water. A DSC of the Stage I material shows little or no Group 1 metal remaining within the silica gel. The difference between Stages I and 0 is that the former can be handled in dry air and even quickly transferred in ordinary laboratory air without catching fire or degrading rapidly. When kept under an atmosphere of dry oxygen for hours to days, Stage I material (in contrast to Stage 0 material which reacts which dry $O_2$) is unchanged and produces the same amount of hydrogen gas upon reaction with liquid water as do fresh samples.

Stage I material has many uses in reactive chemistry as an active reducing agent, and is a better reducing agent than the Stage II material described below. It is probably the reagent of choice for both bulk and chromatographic reductions.

Stage II Material

Stage II material of the invention is a Group 1 metal/silica gel composition comprising the product of mixing a liquid Group 1 metal with silica gel under exothermic conditions sufficient to absorb the liquid Group 1 metal or liquid Group 1 metal alloy into the silica gel pores and heating the resulting mixture to a temperature of between about 215° C. to about 400° C. For example, melting sodium in a mixture of sodium and silica gel and heating in a closed vessel at 400° C. overnight causes complete inclusion of sodium in the silica gel pores and forms a Stage II sodium/silica gel composition. Preliminary Pair Distribution Function experiment on sodium Stage II material show the presence of nanocrystalline sodium silicides (a compound of stoichiometry NaSi, e.g. $Na_4Si_4$) in the silica gel composition. There appears to be no sodium metal present.

In the course of heating to between about 215° C. to about 400° C., an exothermic reaction begins and the Stage II material is formed. Stage I material can then be converted to Stage II material. All of the Group 1 metal is incorporated into the silica gel and the air sensitivity of the resulting material is reduced. Higher melting Group 1 metals, e.g. sodium and potassium, typically do not wet the silica gel at temperatures which lead to formation of Stage 0 or Stage I materials. Sodium, potassium and other high melting Group 1 metals then form Stage II materials. The reaction appears to form an alkali metal—silica gel lattice, such as sodium silicide in the example mentioned above. The stability and reactivity of Stage II material, produced by heating Stage I samples, is similar to that of the material formed by heating higher melting alkali metals such as sodium or potassium with silica gel.

As discussed, Stage II materials can be made from either Stage 0 or Stage I materials by heating them in an inert atmosphere slowly or stepwise to 400° C. For the higher melting alkali metals Na and K, the metal can be heated above its melting point in the presence of calcined, outgassed silica gel and then slowly heated to 400° C. with occasional shaking. In a typical heating procedure, the material in a sealed Pyrex Erlenmeyer flask was heated for 1–3 hours each at 150, 200, 250 and 300° C., followed by overnight heating at 400° C. After each heating period the flask was vigorously shaken to prevent undue "clumping". The product is a loose black powder that pours easily when the preparation remains homogeneous. If the heating is too rapid or the molten metal is not mixed with the silica gel vigorously, the product can contain lumps that must be manually crushed.

Figure 5:
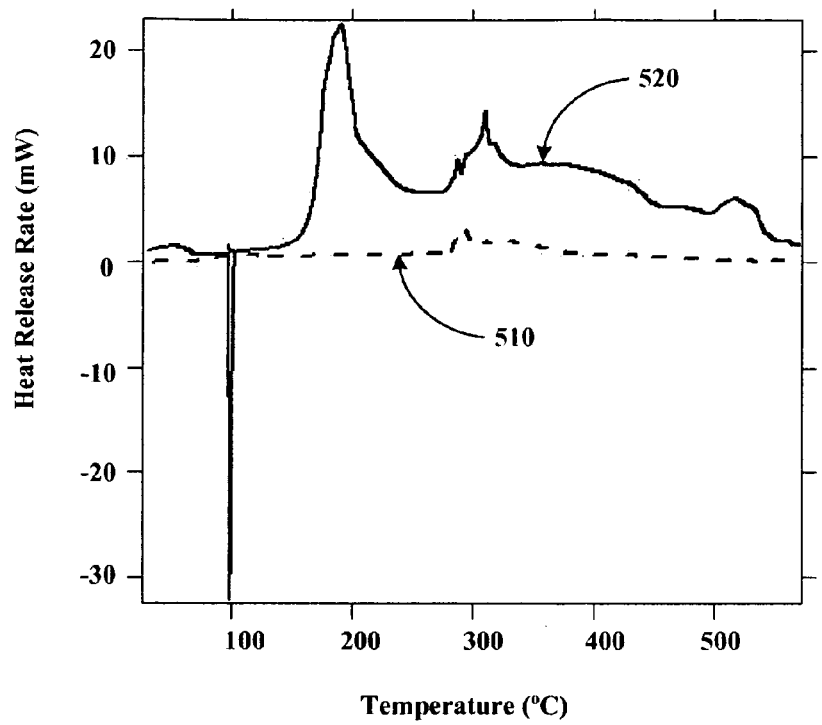
FIG. 5 is a Differential Scanning Calorimetry (DSC) diagram showing traces of 2.4 mg Na mixed with 3.9 mg of silica gel.

The Differential Scanning Calorimetry (DSC) traces of pure Na plus SG are shown in FIG. 5. FIG. 5 illustrates DSC traces for 2.4 mg Na+3.9 mg SG. The overall (exothermic) heat of reaction is about −90±10 kJ/mole Na. Note that the endothermic heat of melting of Na (113 J/g Na), which appears in the initial trace (510) at 98° C., is absent in the repeat trace (520), as are the exothermic peaks. This shows that Na reacted with silica gel during the first run, probably to form the silicide, NaSi. The Stage II reaction of sodium with silica gel releases about 90 kJ of heat per mole of sodium. The melting endotherm of Na metal, present in the initial trace at 98° C., is absent in the subsequent run, showing that the metal has reacted with the silica gel. The reaction products have not been positively identified, but Na plus SG probably forms sodium silicide (of overall composition NaSi) in the 15 nm diameter pores of the silica gel used, with concomitant formation of sodium silicate. X-ray powder patterns indicate that the product is still amorphous.

The Stage II material is an amorphous, matted black powder. The Stage II Group 1 metal/silica gel composition produced does not react with dry $O_2$ or with dry air. Stage II material is easily handled in environments containing dry air. The loose black powders of Stage II material are easily handled in an open ambient environment and do not change with time when kept in the presence of low humidity, such as in a closed container. In fact, the Stage II material is the least reactive of the Group 1 metal/silica gel compositions of the invention. However, this material still reacts rapidly with water to yield almost quantitative amounts of pure hydrogen gas.

Figure 6:
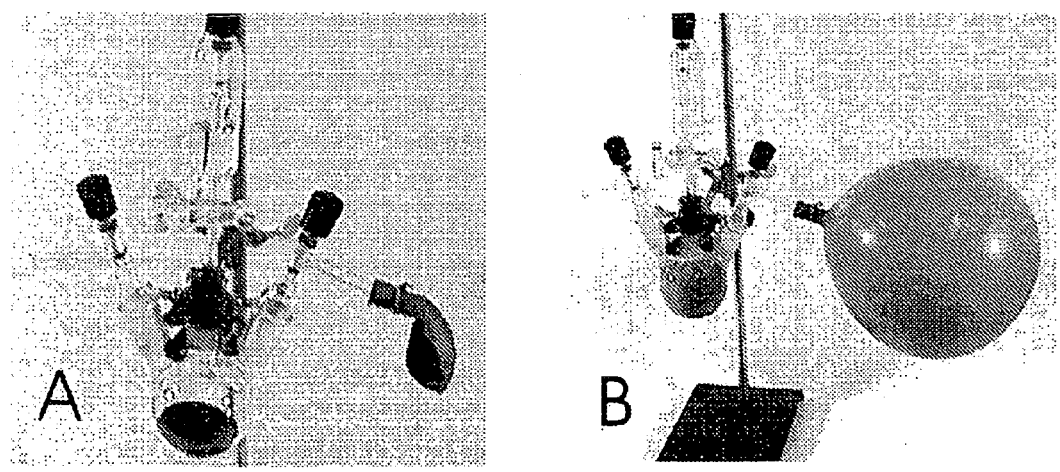
FIG. 6 shows the inflation of a balloon with hydrogen after adding water to style II sodium/silica gel material.

FIG. 6 shows the inflation of a balloon with hydrogen after adding water to a sample of a Stage II sodium/silica gel composition of the invention. The Stage II composition was approximately 30–40% metal by weight. As is shown in image (A), prior to the addition of water, the balloon contains a dry powder under vacuum. Image (B) shows the balloon two minutes after addition of water. The reduced silica gel plus water is still bubbling at this stage. One gram of the powder produces about 170 $cm^3$ of $H_2$ at p=1 atm and 25° C. This material is a convenient, portable source of clean hydrogen upon demand, with the only gaseous products being hydrogen and water vapor.

Although it is the least reactive of the Group 1 metal/silica gel compositions of the invention, the Stage II material has many uses in reactive chemistry, as a passive reducing agent, and for hydrogen production. Stage II material can degrade slowly by picking up moisture from the air, but does not catch fire and can be easily transferred in ordinary laboratory air. The reducing ability does not appear to be as strong as the other stages, but it may be useful in many reductions that do not require the full reducing power of alkali metals. For example, Stage II material can reduce anthracene to dihydroanthracene in the presence of a proton source, but the reduction is slower than with Stage I materials. Because of its insensitivity to ambient air, Stage II material is a preferred reagent for the production of hydrogen by reaction with water.

Stage III Material

Stage III material of the invention is a Group 1 metal/silica gel composition comprising the product of mixing a liquid Group 1 metal with silica gel under exothermic conditions sufficient to absorb the liquid Group 1 metal into the silica gel pores and heating the resulting mixture to a temperature of above about 400° C., and preferably above about 500° C. The Stage III Group 1 metal/silica gel composition produced does not react with dry $O_2$.

As with the preparation of the other Group 1 metal/silica gel compositions of the invention, to prepare Stage III material, the Group 1 metal is mixed with the silica gel under an inert atmosphere or vacuum. In a preferred method, the mixture is first heated to approximately 215° C.–400° C., (forming Stage II material) and then slowly heated to approximately 400° C.–600° C. over several hours. As the temperature is increased above 400° C., a sharp exotherm occurs. The reaction appears to form an alkali metal—silica gel product that contains a silicon rich silicide. The Stage III material is an amorphous, matted black powder that does not react with dry air. If the reaction is to be carried to Stages II or III by heating, the exothermic nature of the reaction would indicate that any large-scale preparations would need a provision for heat removal in order to prevent a "runaway" thermal reaction. In addition, heating can release alkali metal vapor if mixing is not efficient. Thus, as would be appreciated by those skilled in the art, a closed system is likely required for large scale productions.

The Stage III material may have many uses in reactive chemistry, as a doping material, and for hydrogen production.

As discussed above, the various stages of the Group 1 metal/silica gel compositions of the invention may be prepared in sequence for each successive stage. For example, adding a 1:1 mole ratio of sodium and potassium (liquid) to silica gel at 25° C. results in the formation of a free-flowing black powder, a Stage 0 material. In this case, subsequent heating in a closed vessel at 400° C. overnight caused further reaction to produce a less reducing powder, Stage II material. Further heating above 400° C. causes further reaction and produces Stage III material. The Differential Scanning Calorimetry (DSC) traces shown in FIG. 1 indicate that the exothermic reaction of NaK with silica gel occurs in at least two steps. In FIG. 1, a Differential Scanning Calorimetry (DSC) shows traces of a 1:1 NaK/silica gel sample (8.9 mg), wherein the top trace (110) is for a fresh room temperature sample and the bottom trace (120) is a repeat run after cooling the sample. The inset (130) is an enlargement of the low temperature region of the first trace showing a melting endotherm that corresponds to about 50% of the added metal. The total value of ΔH for the exothermic processes corresponds to between −100 and −125 kilojoules per mole of metal.

Figure 2:
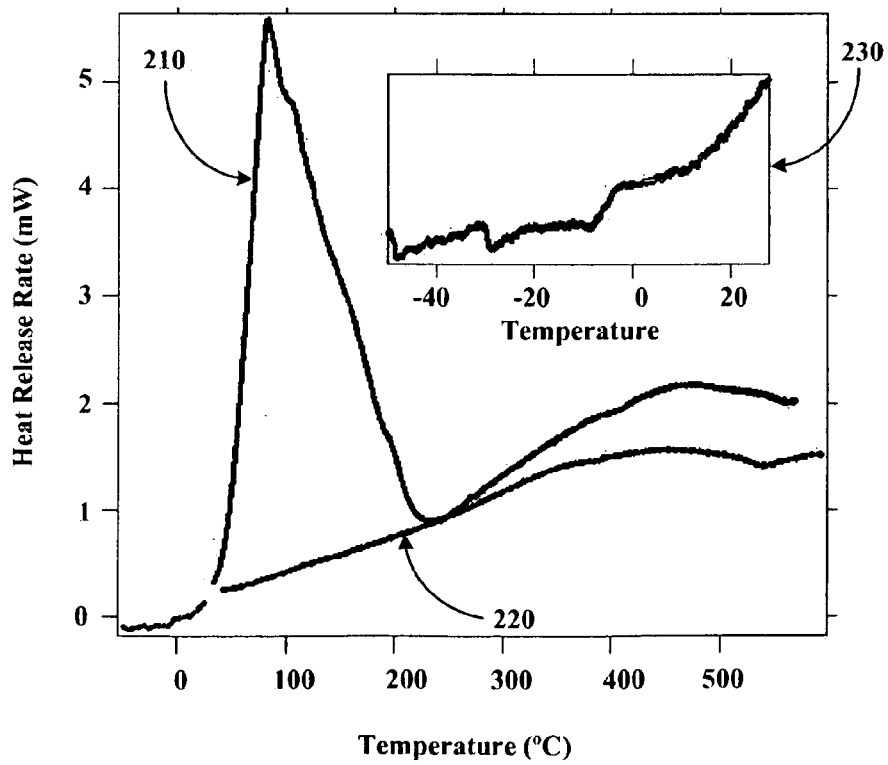
FIG. 2 is a Differential Scanning Calorimetry (DSC) diagram showing traces of a 1:1 $Na_3K$/silica gel sample (5.7 mg).

FIG. 2 shows similar behavior for a Group 1 metal/silica gel composition prepared with $Na_3K$ and an equal mass of silica gel. In FIG. 2, a DSC diagram shows traces of a 1:1 $Na_3K$/silica gel sample (5.7 mg), wherein the top trace (210) is for a fresh room temperature sample and the bottom trace (220) is a repeat run after cooling the sample. The inset (230) is an enlargement of the low temperature region of the first trace showing a melting endotherm that corresponds to only about 10% of the added metal. The total value of ΔH for the exothermic processes corresponds to between −75 and −100 kilojoules per mole of metal. Stage 0 is produced at or near room temperature without significant heat production. Stage II forms spontaneously upon heating to 215–400° C., and Stage III is the final product obtained by heating at to 400–600° C.

Reaction Chemistry of the Group 1 Metal/Silica Gel Compositions

All Group 1 metal/silica gel compositions of the invention react with water exothermically to produce hydrogen in essentially quantitative yield based on the Group 1 metal. Thus, advantageously, the compositions of the invention retain the reactivity of the Group 1 metal. Stage 0 material can be handled briefly in dry air, but it reacts slowly with oxygen and rapidly with moisture. By contrast, Stages I, II and III of the Group 1 metal/silica gel compositions are completely unreactive towards dry oxygen.

Although the Stage I, II, and III Group 1 metal/silica gel compositions of the invention are relatively innocuous and not violently reactive, they do have a strong base present and forms alkali metal hydroxides upon reaction with water. When the metal content is high (about 35% or above) the reaction product with water is completely soluble, probably as the basic metal silicate. Neutralization with acid precipitates silica.

Each stage of the Group 1 metal/silica gel composition of the invention may be used as a reducing agent reacting with a number of reducible organic materials in the same manner known for alkali metals and their alloys. For example, the Group 1 metal/silica gel compositions may be used to reduce aromatic compounds to their radical anions as is common in the so-called Birch reductions, commonly carried out with alkali metal—ammonia solutions. A Birch reduction is a general method of reduction of aromatic compounds by alkali metals in liquid ammonia. The theoretical and preparative aspects of the Birch reduction have been discussed in several reviews. See, G. W. Watt, *Chem. Rev.*, 46, 317 (1950); A. J. Birch, *Quart .Rev.* (*London*), 4, 69 (1950); A. J. Birch and H. F. Smith, *Quart. Rev.* (*London*), 12, 17 (1958); and C. D. Gutsche and H. H. Peter, *Org. Syntheses*, Coll. Vol. 4, 887 (1963). The Group 1 metal/silica gel compositions of the invention can be readily substituted for the sodium in Birch reductions. Example 10 shows a Birch reduction using a Group 1 metal/silica gel composition of the invention.

Similarly, violent reductions such as the Wurtz reduction of halogenated organic compounds such as PCB's might be carried out under controlled conditions. The Wurtz reaction is the coupling of two organic radicals (R) by treating two moles of the organic halides (RX) with two moles of sodium:

2RX+2Na→R—R+2NaX

See A. Wurtz, *Ann. Chim. Phys.* [3] 44, 275 (1855); *Ann.* 96, 364 (1855); J. L. Wardell, *Comp. Organometal. Chem.* 1, 52 (1982); W. E. Lindsell, *ibid.* 193; B. J. Wakefield, *ibid.* 7, 45; D. C. Billington, *Comp. Org. Syn.* 3, 413–423 (1991). The Group 1 metal/silica gel compositions of the invention can be readily substituted for the sodium in a Wurtz reaction or other such dehalogentation reaction. Compositions of the invention have also been used to dehalogenate inorganic halides. Example 11 shows a Wurtz reduction using a Group 1 metal/silica gel composition of the invention.

Industrially useful reactions as desulfurization of petroleum might be carried out with Group 1 metal/silica gel compositions of the invention. As an example, the compositions of the invention may be used in an improved method of removing sulfur from phenyl sulfide to produce biphenyl. The improvement comprises carrying out the following reaction:

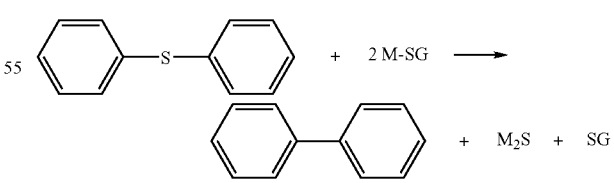

where M—SG is a Group 1 metal/silica gel composition of the invention.

Use of the Group 1 metal/silica gel compositions of the invention allow alkali metal reactions such as those described above to be carried out under safer conditions due to the safer handling of the compositions over the corresponding alkali metal or alloy. Use of the compositions also generally gives higher yields than the corresponding reaction with just the Group 1 metal.

Because Stage I material (such as a Stage I Na$_2$K/silica gel composition) is very easy to prepare and retains much of the reducing ability of the parent Group 1 metal, it is likely to find use as a powerful and convenient reducing agent. Small glass columns filled with the Stage I powder are able to reduce a variety of organic compounds when they are dissolved in tetrahydrofuran (THF) and passed through the column. Alternatively, batch reactions can be carried out simply by stirring THF solutions of the organic compounds with the Stage I material. For example, as is shown below, benzophenone (1) is reduced to the radical anion (ketyl); benzyl chloride (2) undergoes Wurtz reduction to form bibenzyl (3), and dibenzothiophene (4) is reduced to the radical anion and ultimately to a mixture of products that are free of the starting material. Other reactions include the Wurtz reduction of dichlorobenzene to form the expected coupling products and the Birch Reduction of anthracene to dihydroanthracene.

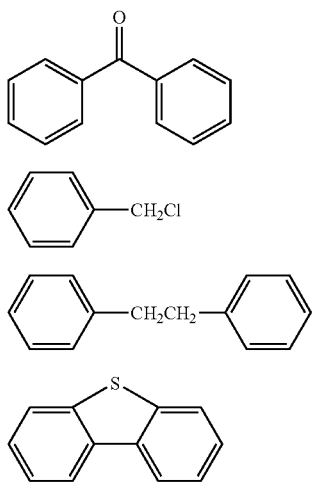

Stage II sodium/silica gel composition, as noted above, is easier to handle in air than Stage I material. Its production of hydrogen by reaction with water is quantitative and it is also able to carry out many of the organic reductions described above for the Stage I material. For example, it can reduce benzophenone (1) to the radical anion and it can convert benzyl chloride (2) to bibenzyl (3). Numerous other reactions of Stage I and II materials are possible and likely. The reduction of the representative compounds discussed above indicate that the Group 1 metal/silica gel compositions of the invention can reduce aromatic compounds to the radical anions or dianions, break carbon-sulfur bonds, and completely dechlorinate aromatic chlorides. This material might therefore be able to destroy PCB's by dechlorination and carry out desulfurization reactions. The powerful reducing properties of the Group 1 metal/silica gel compositions also permit the use of chromatographic columns packed with this material for the reduction of organic and inorganic compounds that are now reduced by Na-K or alkali metal-ammonia solutions.

A major use for all four stages of reduced silica gel compositions of the invention is in the fuel storage potential and the formation of hydrogen gas needed for mobile fuel cells. For example, large stocks of the reduced silica gel powder might be kept on conveyor trays within a holding tank. Addition to water would liberate pure hydrogen gas plus water vapor. All stages produce near quantitative amounts of the hydrogen that would have been produced from the alkali metal used. The hydrogen could then be used to power mobile fuel cells. For example, stocks of the Group 1 metal/silica gel compositions might be kept on conveyer trays within a holding tank. Water is then introduced and the mixing with the water would liberate hydrogen which can then be extracted and compressed or pressurized. The compressed hydrogen would be used to fill mobile fuel cells. The spent powder, at this stage is now just silica gel or dissolved metal silicate that could be reactivated with new Group 1 metal or used for other purposes.

Another embodiment of the invention relates to the use of silica gel to clean up Group 1 metal spills and similar remains from spent operations. This embodiment takes advantage of the absorptive nature of the silica gel discussed above in the preparation of the compositions of the invention. As described in example 8, upon performing experiments with cesium metal in the glove box, several grams of the cesium was spilled onto the box floor. Kimwipe tissues were first used to clean up the spill, but the dirty wipes would ignite once removed from the helium filled glove box. It was then decided to try and absorb the cesium using silica gel hoping to make it stable enough to make it from the box to a safe place for disposal before ignition in air. This lead to the use of silica gel to clean up metal or other spills, in particular reactive metals such as alkali metals, where the metal was a liquid or could be melted to form a liquid. When dealing with high melting alkalis, the metals must be heated to a liquid state for cleanup to occur.

Compositions using alkali metals, e.g. sodium, potassium, etc., deliver active substances, e.g. to vaporize fragrances in deodorizer compositions, are described in U.S. patent application Ser. No. 10/248,765, "System for Delivery of Active Substances", which is incorporated herein by reference. Due to their stability the Stage I, II and III compositions of the invention and compatible with such active ingredients, e.g. fragrances. In yet another embodiment, the invention also relates to a such compositions containing Group 1 metal/silica gel compositions of the invention. For example, the deodorizer composition may contain about 5 to 15 weight percent of a reduced silica gel of the invention, 10 to 30 weight percent of a fragrance, and up to about 75 weight percent of a neutralizer and/or organic acid. In addition to the fragrance, a deodorizer may also contain other active ingredients such as disinfectants, surfactants, and colors or dyes. The reaction of the Group 1 metal/silica gel composition with water distributes the fragrance or other active ingredient.

EXAMPLES

Example 1

An exemplary silica gel, Davisil 30 to 50 mesh, was obtained from Grace-Davison as a free-flowing powder that is listed as 99+ percent SiO$_2$. However, it contains large amounts of gaseous material, probably water and air. In order to remove the gaseous material the silica gel was heated under vacuum in an evacuable Erlenmeyer flask, first with a hot air dryer and then with a torch. The estimated temperature reached approximately 300° C. As discussed

Example 2

One significant feature of the Group 1 metal/silica gel compositions of the invention is their ability to produce pure hydrogen gas quantitatively upon addition to water. The "reducing power" of the Group 1 metal/silica gel compositions was determined by adding water to an evacuated sample and collecting hydrogen with a modified Toeppler pump. The reducing power is defined as the weight percent of alkali metal or alloy used that would produce the same amount of hydrogen. This was verified by collecting the hydrogen produced from a known mass of material upon reaction with out-gassed water. The hydrogen was collected in a calibrated pipette using a modified Toeppler pump (mercury filled). The amount of hydrogen produced was generally equivalent to the amount that would have been produced by the metal(s) alone. Such analyses were run on every sample of reduced silica, regardless of the stage of the material. For example, if a 40 wt % sample of NaK in Stage I silica gel produced the same amount of hydrogen as would be produced by that amount of NaK alone, the reducing power would be 40%. The total amount of alkali metal hydroxide formed was then determined by the addition of HCl and back-titration with sodium hydroxide. The difference between the total alkali metal percentage as obtained from the titration and the reducing power is presumably a measure of the concentration of SiOH groups and other sources of hydrogen. Alkali metals can react with such groups during sample preparation to release hydrogen. This reaction is presumably the origin of the detectable amounts of gas formed during the mixing of the metal or alloy with the silica gel.

Example 3

Using a stainless steel pan inside of a helium filled glove box, 14 g of outgassed and calcined silica gel was mixed with 9.7 g of $Na_2K$ from a Pasteur pipette to create Stage 0 material. The $Na_2K$ was added drop wise to various regions of the silica gel coated pan. The drops of alloy wet the silica gel and could be "squashed" with a spatula to aid the alloy inclusion. The product never got warm and appeared to have a very shiny surface indicating free metal on the surface. It appeared that the $Na_2K$ was not completely absorbed into the silica gel pores. The sample was then setup for Differential Scanning Calorimetery (DSC) by putting 3.6 mg of the sample into a DSC pan. The DSC was run from ~−55 to 60° C., held for ten minutes, and then re-run. After, the sample was run to 450° C. twice. The endotherm of melting corresponded to ~135 J/g metal, which is slightly higher than expected based on metal added. The weighed mass could be off or we could have inhomogeneities in concentration. When heated to 60° C. and held for ten minutes and then repeated gave a $\Delta H_{melt}$=61.4 J/g metal showing an annealing effect is already present to convert to sample to the next stage. The "reducing power" of the sample was determined by adding water to an evacuated sample and collecting hydrogen in a modified Toeppler pump. The reducing power is defined as the amount of Group 1 metal that would be required to produce the same amount of hydrogen. A $H_2$ evolution from 21 mg of the same sample yielded 37% reducing power. This is in agreement with the nominal 40 wt % metal concentration.

Example 4

Figure 7:
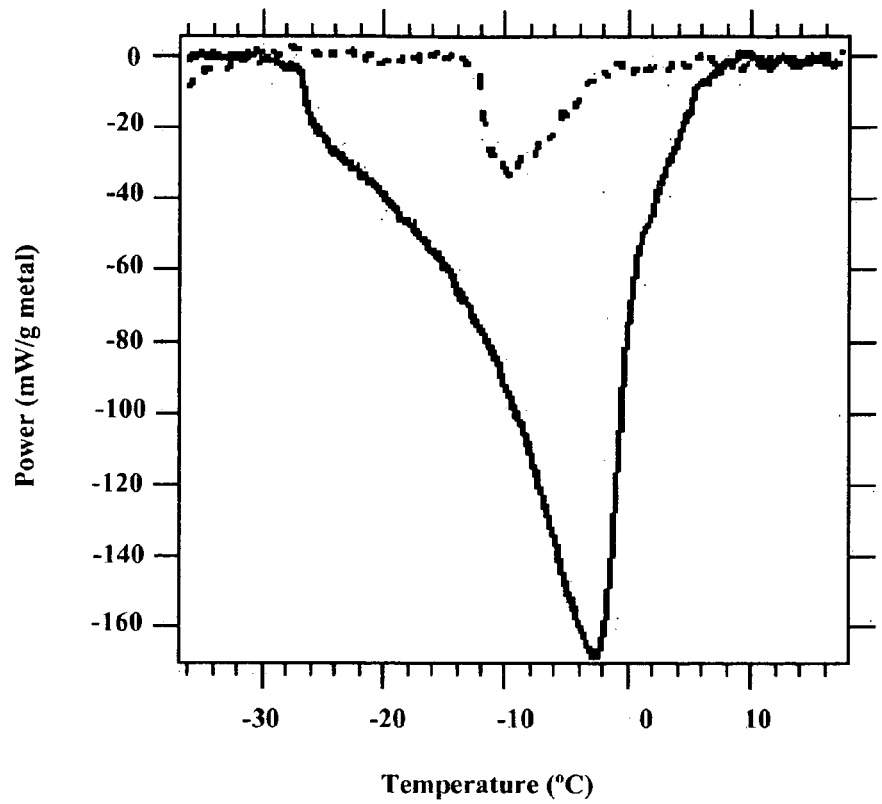
FIG. 7 is Differential Scanning Calorimetry (DSC) diagram showing the results of heating Stage 0 material overnight at about 140° C. in vacuo or in an inert atmosphere.

The conversion of Stage 0 material to Stage I material can be performed by both aging the sample or by uniform heating. Simply heating Stage 0 material overnight at about 140° C. in vacuo or in an inert atmosphere while mixing converted it to the Stage I form that shows little or no melting endotherm by DSC (See FIG. 7). Because of the small particle size, Stage 0 material starts to melt at −25° C. rather than at the bulk onset temperature of −13° C. The small value of ΔH (9 J/g metal) for Stage I material compared with 117 J/g metal for Stage 0 shows that most of the metal is probably converted to alkali metal cations. The apparent absence of free alkali metal in the pores or on the surface of the silica gel particles makes this stage totally free of oxidation in dry air.

Example 5

The preparation of Stage II material can be performed by continuous heating of Stage 0 and Stage I materials to 400° C. or by using the higher melting alkali metals, such as sodium and potassium. Outgassed and calcined silica gel 13.5 g, was weighted out and about 7.3 g of Na metal was added. The silica gel was outgassed with heating to a pressure of $3.5 \times 10^{-5}$ torr. The combination of silica gel and Na was heated first to 150° C. for 1 hr, then shaken vigorously, then heated to 200° C. for 1.5 hrs. The material was shaken vigorously approximately every 30 minutes. Lastly, the material was heated to 300° C. overnight. The powder looked loose and free flowing. The temperature was then raised to 400° C. and the material was heated 3 more hours.

Example 6

In preparation for NaK inclusion into silica gel, 3.00 g of 600° C. calcined silica gel was placed in an Erlenmeyer flask with 3.012 g of NaK. The NaK alloy was made with 5.562 g of Na and 9.433 g of K. This mass of NaK has about 50 mmol each of Na and K and 50 mmol of $SiO_2$. Therefore, a 2:1 mole ratio of metal to Si was used in the sample. At room temperature, the silica gel began to turn black and went to a uniform, pourable shiny black powder within several minutes without any noticeable exothermicity. From the sample, 22.6 mg were removed for $H_2$ analysis. The $H_2$ evolution was performed at T=296.6 K and $P_{atm}$=738.9 Torr. After evolution, there was 176.5 μmol $H_2$ corresponding to 353 μmol of metal. This $H_2$ evolution corresponds to 48.4 wt % of metal in the silica gel, nominally the 50 wt % initial loading. The sample can then be heated through a controlled process to achieve Stage I and II material. It should be noted, however, that heating the flask during preparation can initiate a strongly exothermic reaction causing the metal to "bump" and coat the vessel.

Example 7

A number of different preparations with varying amounts of metal+silica gel were prepared that had alkali metal concentrations of 20 to 50 weight %. One sample was prepared with Na and silica gel loaded to a 45.6% reducing power. The reducing power was generally 94% or more of the maximum that could be obtained based on the amount of metal added. The remaining 2–6% represented reaction of the alkali metal(s) with defect sites. The measurement of the reducing power after various treatments such as exposure to above, silica gel can be out-gassed more easily (with passivation of active sites) by heating the material to 600° C. or hotter in air (calcination).

oxygen or heating was used to provide information about the stability of this material. In 48 hrs, the reducing power decreased to only 44%, a total loss of 1.6%, indicating almost no reaction with oxygen in the absence of moisture. It is possible to use other alloys with different ratios of Na to K that are a liquid at or near room temperature. For example, we have prepared a reduced silica using Na$_3$K with results similar to that described in Example 5. The sample was prepared by adding 8412 mg of silica gel to 433 mg of Na$_3$K in an Erlenmeyer flask in a helium-filled glove box. Two other samples with a 1:1 mass ratio of NaK to silica gel have also been prepared. Lastly, a sample was prepared with a 1:4 mass ratio of NaK to silica gel. All of these samples formed Stage I free-flowing black powders that are stable in dry air. Long term storage in the glove box resulted in no detectable change in properties.

Example 8

We had a liquid Cs spill within the helium glove box. This led us to discover an effective clean-up process for alkali metals. Silica gel was poured upon the Cs spill and was mixed around with a Kimwipe. All of the Cs metal was absorbed into the silica gel turning the silica gel a black color. Thus, silica gel makes an ideal clean-up material for low melting alkali metals and eutectic alloys, such as NaK.

Example 9

Figure 3:
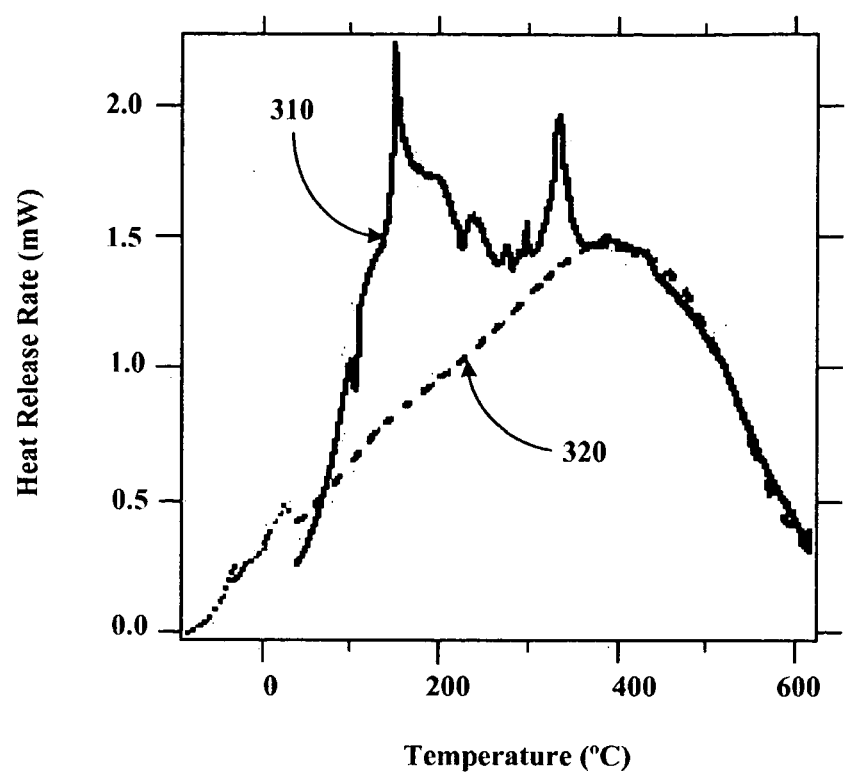
FIG. 3 is a Differential Scanning Calorimetry (DSC) diagram showing traces of a 1:1 cesium/silica gel sample (6.7 mg).

The behavior of pure cesium was similar to that of NaK alloy, as shown in FIG. 3. In FIG. 3, a DSC diagram shows traces of a 1:1 cesium/silica gel sample (6.7 mg), wherein the top trace (310) is for a fresh room temperature sample and the bottom trace (320) is a repeat run after cooling the sample. The total value of ΔH for the exothermic processes corresponds to about −120 kJ/mol metal. Note the absence of a melting exotherm of Cs metal. But, since 50 wt % Cs contains less than 0.5 moles Cs/mol silica, no melting endotherm of Cs metal was observed in the DSC experiments. Four samples of cesium-loaded silica gel have been prepared; two were prepared by vapor-phase addition and one by the direct addition of cesium metal to the silica gel. All three preparations formed free-flowing powders. The two vapor-phase additions were prepared at room temperature and 40° C., respectively. Light loadings of cesium, <20 wt %, by vapor-phase addition formed reduced silica that was blue in color. Higher concentrations yielded free-flowing black powders. Heating Stage I material formed Stage II and/or Stage III reduced Cs-containing silica gel with the evolution of heat. For example, FIG. 3 shows the DSC result of heating 1:1 Stage I Cs-silica gel to 650° C. and then reheating the cooled sample. It can be seen that the first heating resulted in an exothermic reaction that was not present in the reheated sample. This shows the conversion of Stage I material to Stage III and the absence of further significant reaction of the Stage III material.

Example 10

Figure 8:
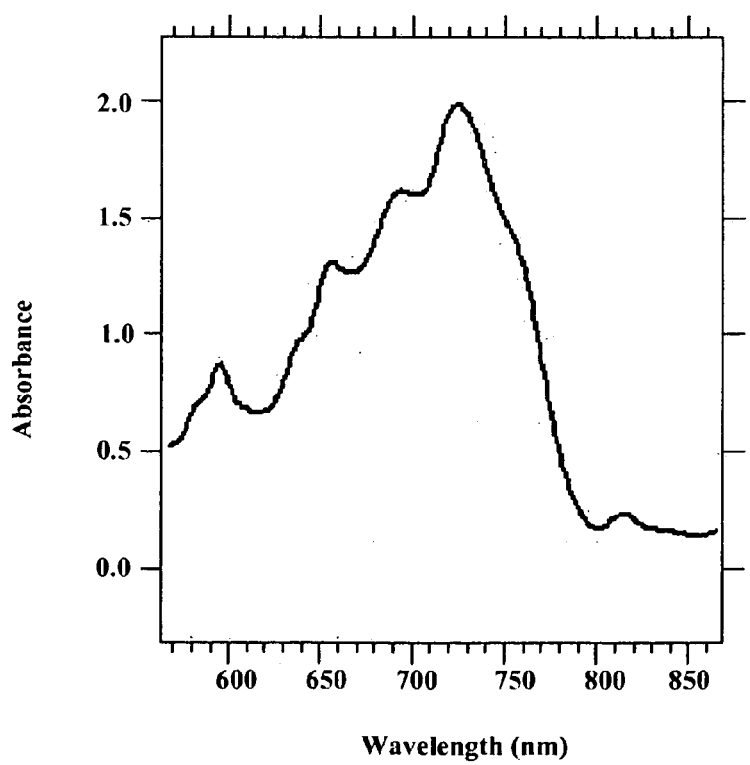
FIG. 8 shows an optical spectrum of an anthracene radical anion obtained by the reduction of anthracene with the Stage I material of the invention.

All of the alkali metal-silica gel powders, from Stage 0 to Stage II, are able to reduce anthracene to the radical anion by Birch reduction. The reduction was observed by the formation of an intense blue color of the solution and verified by obtaining the optical absorption spectrum of the product (See FIG. 8). FIG. 8 shows an optical spectrum of an anthracene radical anion obtained by the reduction of anthracene with the Stage I material of the invention, M—SG. This is essentially the same as the known spectrum of this anion. This radical anion is stable enough to persist in solution for many hours. This reaction can be performed using several reaction setups, such as a batch reaction, a layered (alkali metal-silica gel layered on top of commercial silica gel) chromatographic column, and a mixed (alkali metal-silica gel uniformly mixed with commercial silica gel) chromatographic column, typically 50:50 ratio of materials. Either the layered- or the mixed-bed chromatography column could be used with the alkali metal-silica gel to reduce anthracene and protonate the resulting radical anion with its retained water. The product is 9,10 dihydroanthracene as expected. The reaction may be illustrated as is shown below.

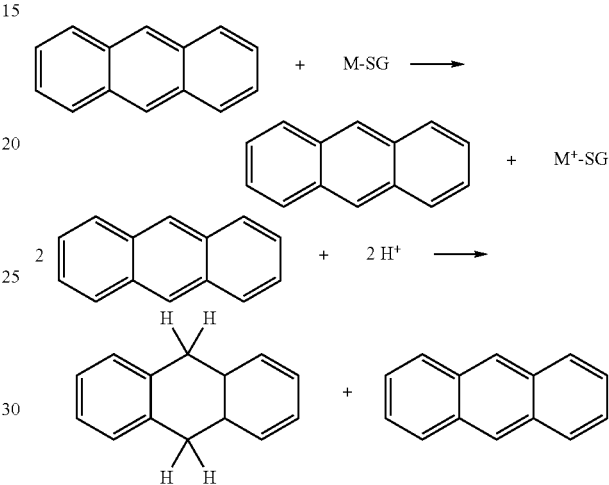

Figure 9:
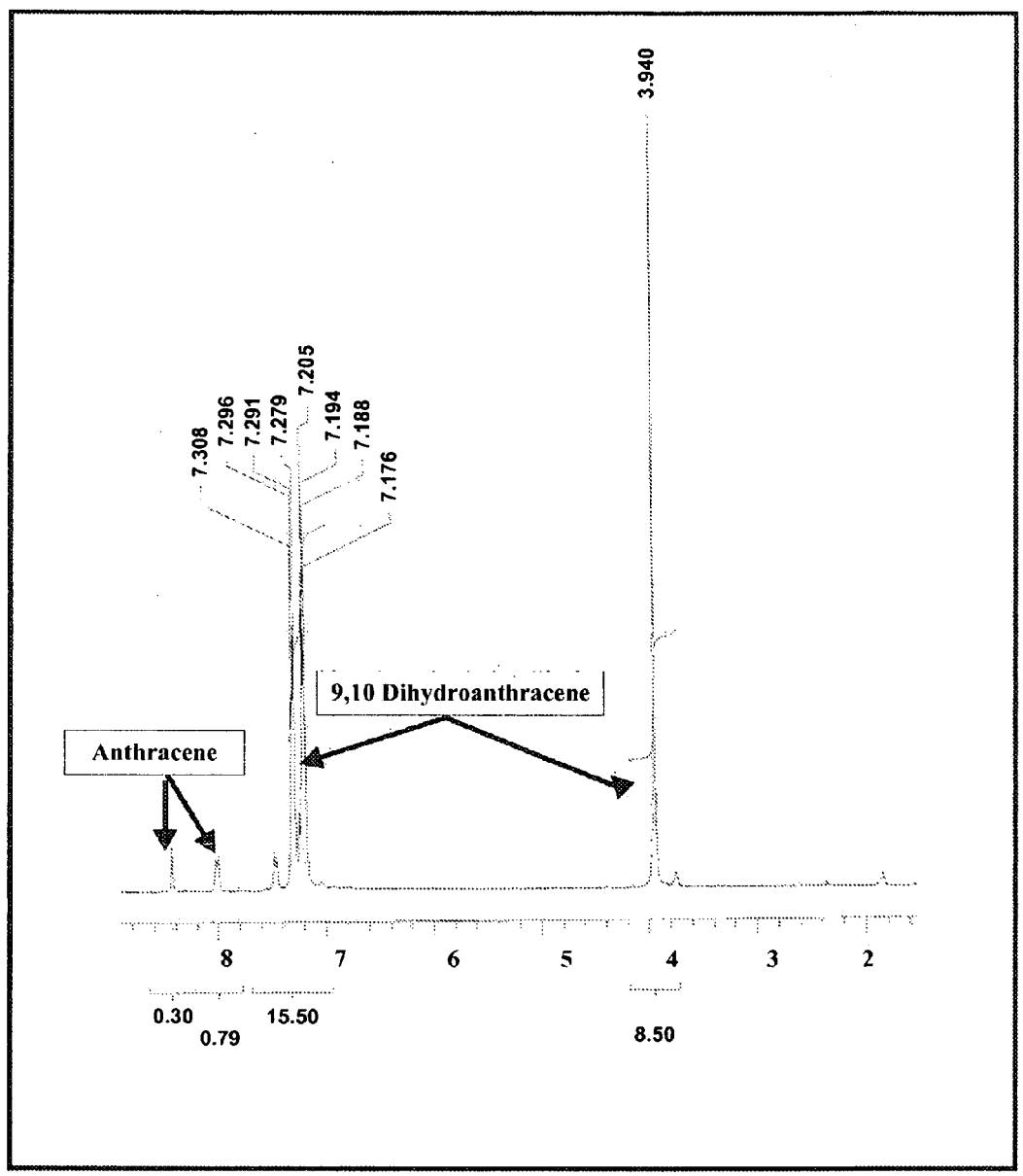
FIG. 9 shows a $^1H$ NMR spectrum of the product of a Birch Reduction of anthracene in THF by passage through a mixed bed column of the Group 1 metal/silica gel composition of the invention.

FIG. 9 shows a $^1$H NMR spectrum of the product of a Birch Reduction of anthracene in THF by passage through a mixed bed column of the Group 1 metal/silica gel composition of the invention. The yield in this case using Stage I material was 92% of the desired product and the total elution time was less than two minutes. Further experimentation resulted in a 100% yield. This illustrates the efficiency of the Birch reduction for a reactant that readily forms a radical anion. The GC-MS analysis of a bulk reaction product that had been protonated with t-butanol showed primarily only anthracene and 9,10 dihydroanthracene. It should be noted that column chromatography with Stage II material instead of Stage I material yielded less product, indicating that reduction is slower with this less reactive reduced silica gel. The data in Figures for the reaction with a Stage I Na$_2$K/silica gel material, (~30–40 wt % Na$_2$K).

Example 11

Figure 10A:
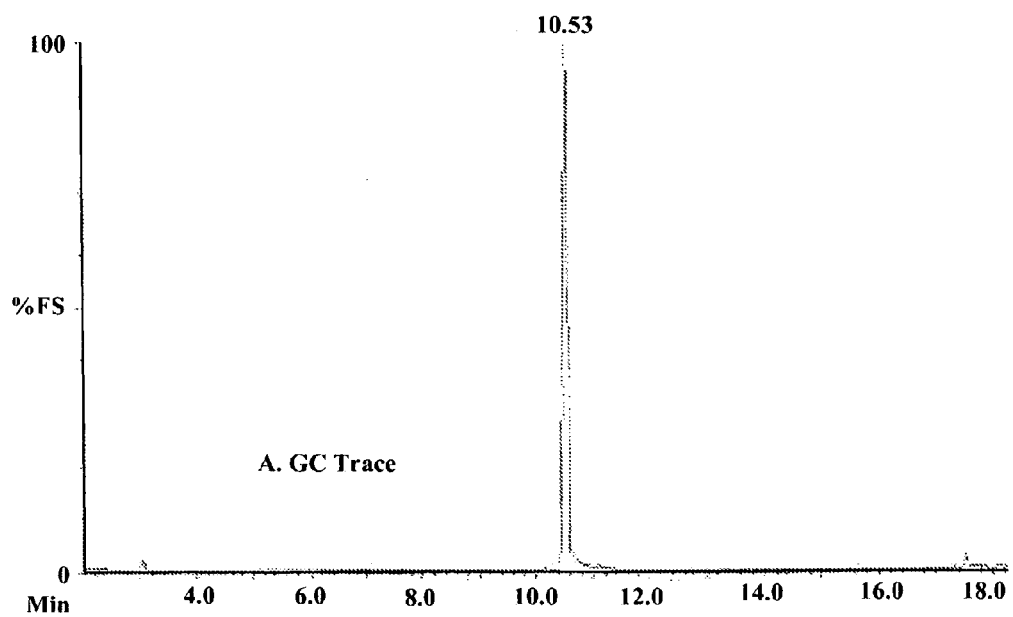
FIGS. 10A–10C show the results of an analysis of the product of reduction of benzyl chloride in a batch process.
Figure 10B:
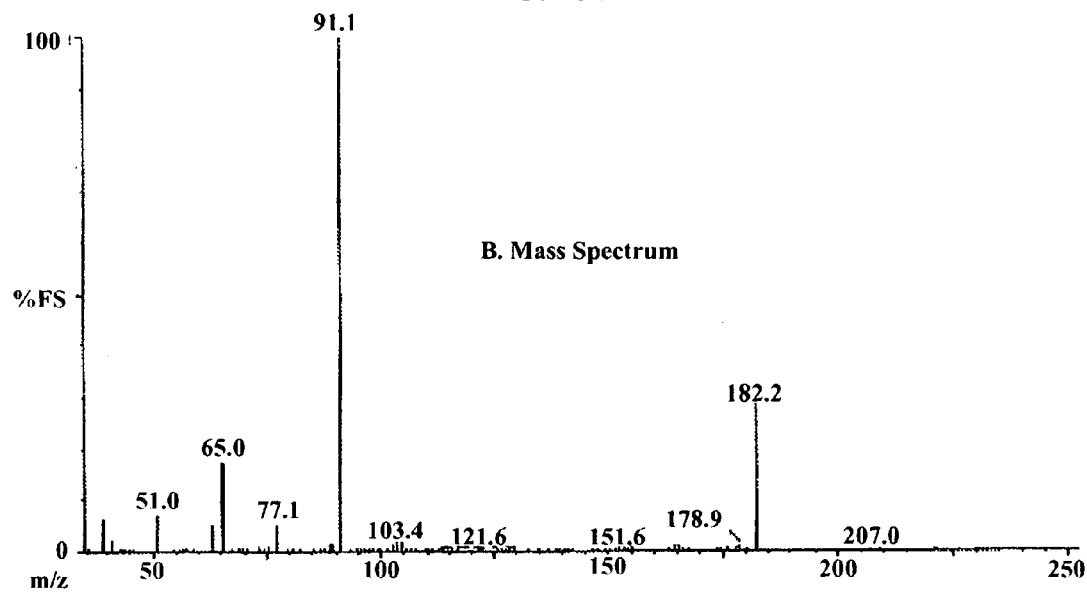
Figure 10C:
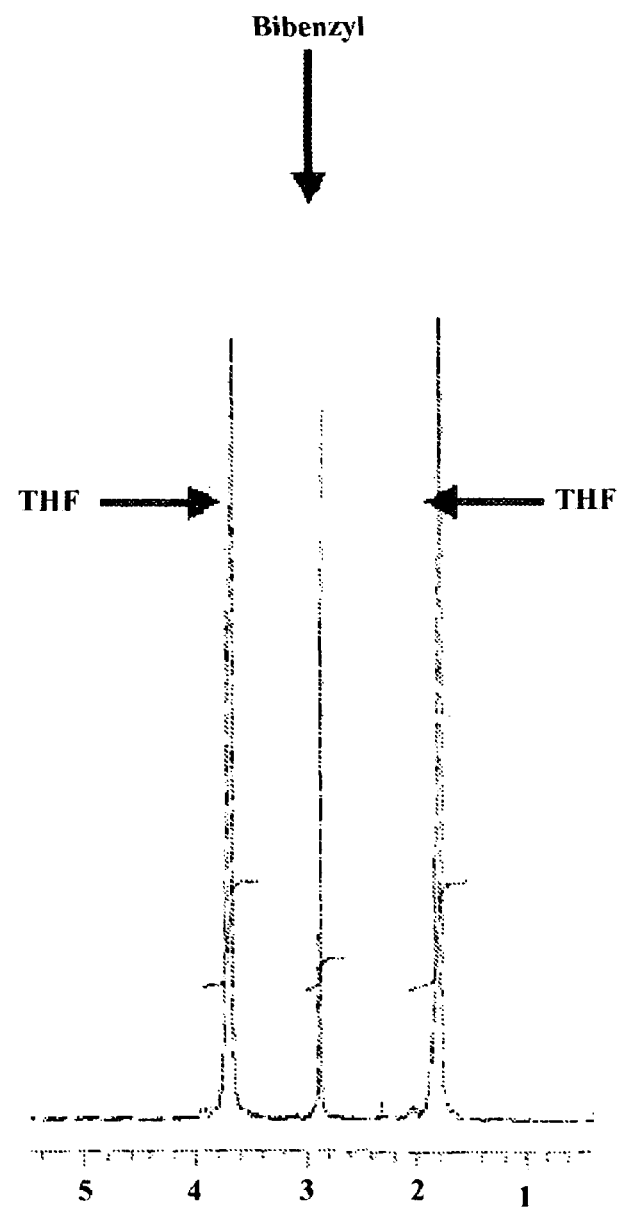

One of the earliest reactions of alkali metals with organic compounds is the Wurtz reaction in which de-halogenation of a chlorocarbon results in coupling to form a new carbon-carbon bond. When used with a bulk alkali metal and the neat chlorocarbon however, the reaction can be dangerously explosive. As is shown below, this coupling reaction was carried out with ~130 mg of benzyl chloride dissolved in 10 ml of THF by reduction with ~1.3 g of Stage I Na$_2$K/silica gel material (~30–40 wt % Na$_2$K). Partial reduction (~30%) occurred upon rapid passage through the small column. However, further experimentation resulted in a complete, 100% yield when using Stage I and Stage 0 Na$_2$K/silica gel materials (~30–40 wt % Na$_2$K) upon rapid passage through the column. Therefore, speed of column pass through will vary the extent of reactant conversion to desired product. Bulk reduction had occurred after 3 hours of stirring with the Stage I Na$_2$K/silica gel material. The only product detected by both GC-MS and $^1$H NMR was bibenzyl (See FIGS. 10A–10C). FIGS. 10A–10C show the results of an analysis of the product of reduction of benzyl chloride in a batch process. FIG. 10A shows a single line GC trace, FIG. 10B shows a mass spectrum of GC product, and FIG. 10C shows a $^1$H NMR of the product. The MS shown in FIG. 10B matches exactly the MS of bibenzyl. Note the complete absence of the peak for the reactant benzyl chloride at 4.6 ppm.

Other dehalogenation include the dechlorination of 1,2 dichlorobenzene (partial through the column, complete in bulk). These tests show that both aromatic and aliphatic halocarbons can be readily de-halogenated by the Group 1 metal/silica gel composition of the invention.

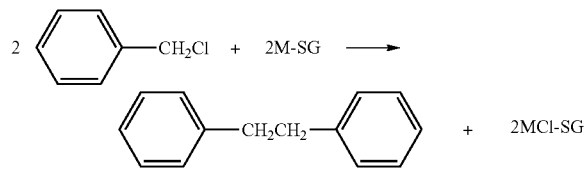

Example 12

Figure 11A:
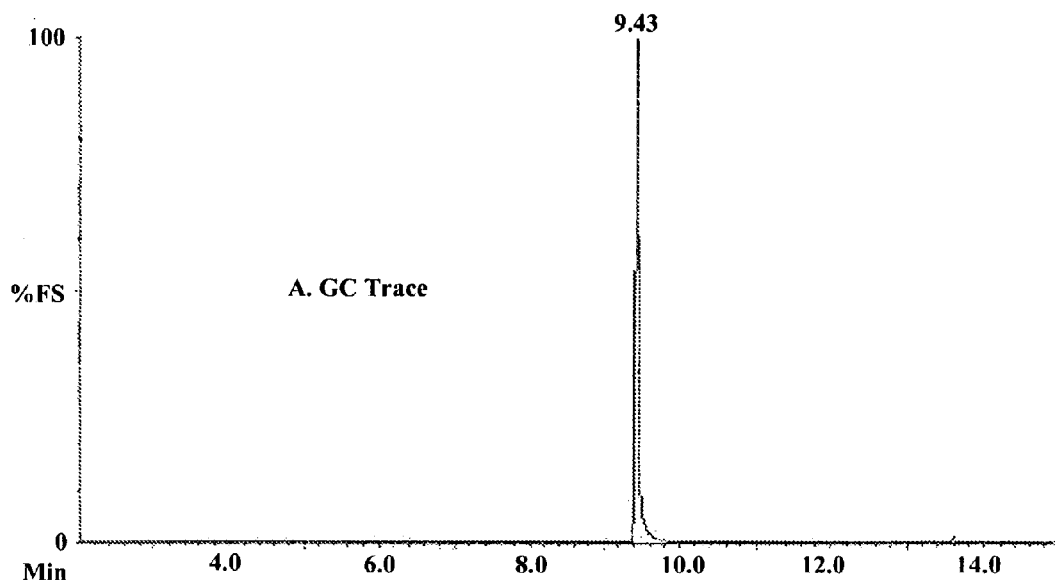
FIGS. 11A–11C show the results of an analysis of the product of an overnight batch reaction of phenyl sulfide with the Stage I material of the invention.
Figure 11B:
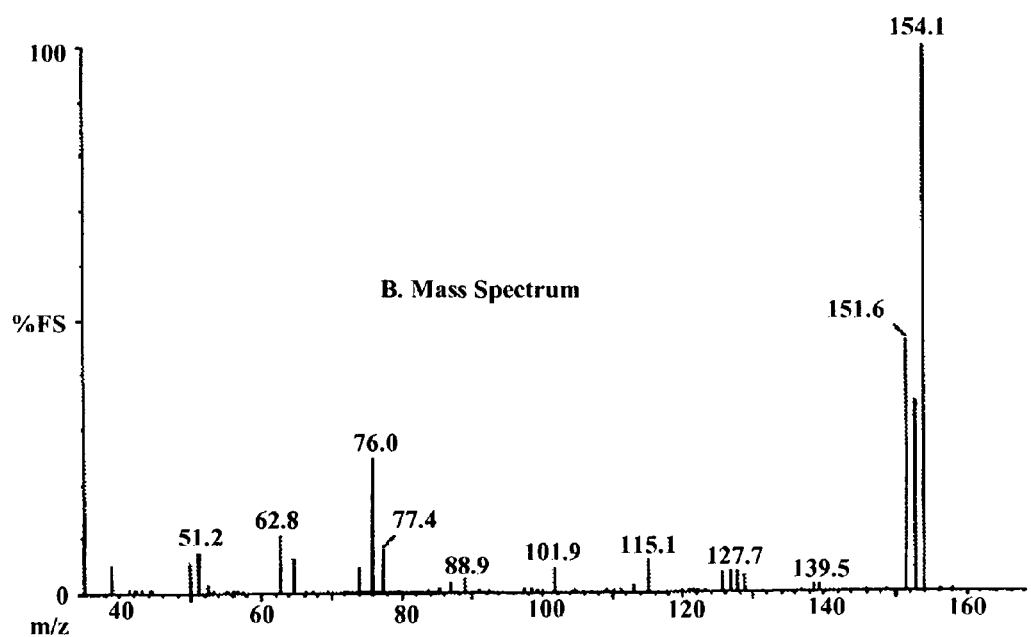
Figure 11C:
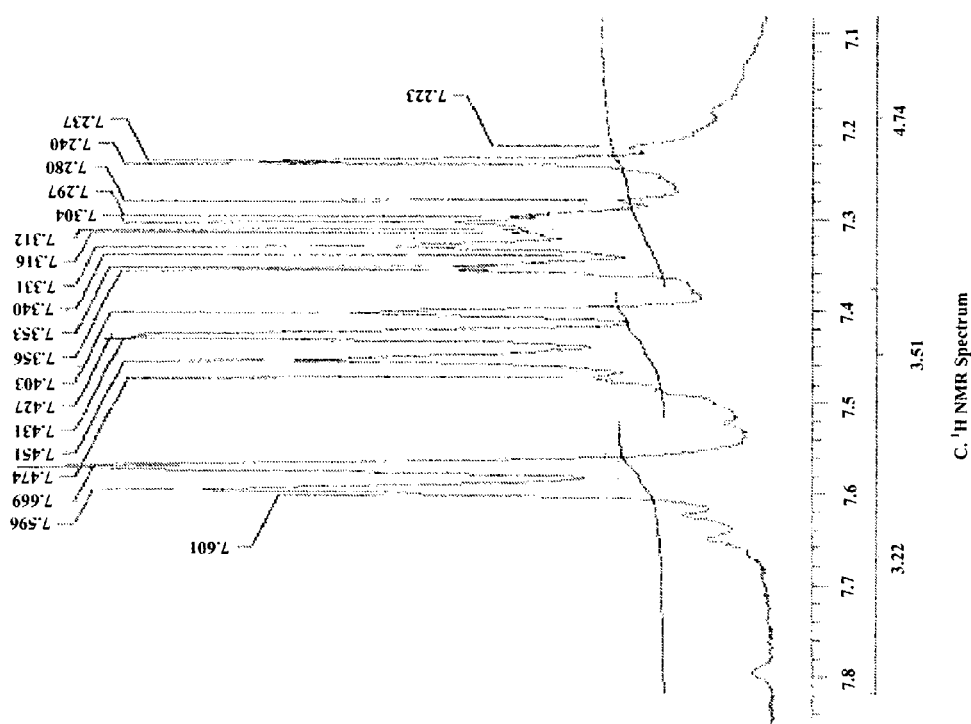

Sulfur elimination from hydrocarbon sulfides can present many problems and yield a myriad of products. It was rather surprising, therefore, that the batch reaction of phenyl sulfide with Stage I Na$_2$K/silica gel (~30–40 wt % Na$_2$K) yielded only biphenyl as a product, as shown below. This was verified by both GC-MS and $^1$H NMR (See FIGS. 11A–11C). FIGS. 11A–11C show the results of an analysis of the product of an overnight batch reaction of phenyl sulfide with the Stage I material of the invention. FIG. 11A shows a single peak GC trace, FIG. 11B shows a mass spectrum of GC product, and FIG. 11C shows a $^1$H NMR of the product. The NMR in FIG. 11C is primarily the NMR spectrum of biphenyl. It also shows the presence of chloroform from the deuteron-chloroform used as well as some phenyl sulfide reactant. The yield cannot be qualified because of NMR overlap in the region of chemical shift at around 7.3 ppm, but the product is mostly biphenyl. Similarly, sulfur was completely removed from dibenzothiophene, a process that is particularly difficult in hydrocarbon desulfurization. Again GC-MS showed the primary product to be biphenyl, although $^1$H NMR showed the presence of other products.

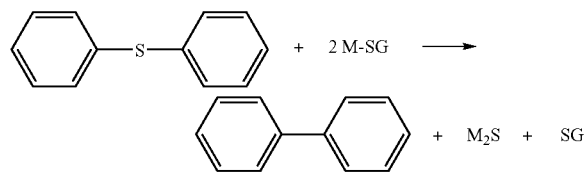

Example 13

An important initial question for the use of the Group 1 metal/silica gel compositions of the invention was whether metallic Group 1 metals are present in the reduced silica composition. To test this, a sample of finely divided sodium and silica gel was prepared. Since the sodium tends to agglomerate easily, it was prepared by evaporating ammonia from a frozen solution of sodium in ammonia. Three portions of this material were tested by differential scanning calorimetry (DSC). The heat absorbed upon melting sodium at 98° C. was used to determine the amount of sodium in the sample. This was followed by broad exothermic peaks between 100° C. and 490° C. There was also a sharp endothermic peak of unknown origin at 280° C. Upon cooling the sample and reheating, no thermal peaks were observed. This shows that heat treatment completely removes free sodium, presumably because of reaction of sodium with the silica. Moreover, solid state Na NMR showed no metallic sodium present in the reduced silica gel composition. Additionally, it was possible to estimate the heat of reaction of the product "reduced silica" with water. The heat of reaction (exothermic) of the reduced silica with water is approximately −136±18 kJ/mol Na, which is about 75% of that of pure sodium. Thus, the Group 1 metal/silica gel compositions of the invention release considerable heat when it reacts with water.

The total amount of sodium hydroxide formed was then determined by the addition of HCl and back-titration with sodium hydroxide. The difference between this result and the reducing power is presumably a measure of the concentration of SiOH groups. The Group 1 metal can react with such groups during the preparation to release hydrogen. This reaction is presumably the origin of the large amount of gas formed during the melting of sodium in the presence of silica gel.

Example 14—Preparation of a 50 wt % Sodium-Potassium Reduced Silica Gel

First, about 40 g of silica gel was heated in air overnight at 600° C. to out-gas the silica gel. 3.0 g of this silica gel was further out-gassed with heating to about 300° C. under high vacuum (2×10$^{-5}$ torr) in an adapted long-neck Erlenmeyer flask. Next, the flask was placed in a helium-filled glove box via an evacuated port. Then 3.0 g NaK (1:1 molar ratio) was added to the flask that contained the silica gel to form a 50:50 mass ratio of silica gel to NaK. At this point the NaK began to wet the silica gel surface turning the silica gel black. After removal from the glove box, the flask was evacuated to approximately 2×10$^{-5}$ Torr. A small amount of agitation provided enough activation for the entire sample to be converted to a free-flowing black powder (Stage I). Upon the reaction, there was no detectable heat release. A second sample, warmed with a heat gun, spontaneously reacted exothermically such that the flask became too hot to touch. Presumably, this converted the Stage I material to another form (Stage II or Stage III).

Example 15—Preparation of Sodium-Containing Reduced Silica Gel

First, 2.25 g of silica gel was heated under vacuum to outgas the silica gel. The flask was then removed from the heat after no more gas evolved and the pressure reached 3×10$^{-5}$ Torr. Next, the flask was then placed in a glove box filled with helium via an evacuated port. After being placed in the glove box, 1.135 g Na was added to the flask. Liquid ammonia (NH$_3$) was then freeze-pumped once and distilled over the Na-silica gel powder, thereby causing the following catalyst decomposition reaction:

$$Na + NH_3 \rightarrow NaNH_2 + \tfrac{1}{2}H_2$$

The line was then incrementally pumped out because of the significant amount of $H_2$ which evolved during the catalyst decomposition reaction. Any remaining $NH_3$ was then removed and the flask was evacuated to $3 \times 10^{-5}$ Torr. Next, the flask was heated with a heat gun under vacuum conditions. After heating, the flask was placed back in the glove box. The sample was then distributed into 5 vials. The first vial (449 mg) was removed from the glove box and was stored at room temperature. The second, third, and fourth vials (509 mg, 603 mg, and 653 mg, respectively) were placed in the glove box freezer. The fifth sample (122 mg) was placed in a sealed vial before being dumped into a 1000 mL beaker of water.

Example 16—Preparation of Sodium-Containing Reduced Silica Gel

First, 2.2786 g of $99^{+}\%$ silica gel (30–50 mesh) was added to an Erlenmeyer flask. The flask was then heated and out gassed under vacuum conditions, first with a heat gun, then with a torch. The torch fuel ($O_2$) was adjusted to give a yellow tip to the torch flame. After heating and out gassing the silica gel, approximately 2.145 g of silica gel remained with a volume of 2.5 cm$^3$. The flask was then heated and pumped to a pressure of $2 \times 10^{-5}$ Torr. After being heated, 980 mg of Na was rolled into cylinders and added to the flask. The target amount of Na was 1.0 g. As the Na melted in the flask, the pressure changed to approximately $10^{-3}$ Torr. The flask was heated intermittently for 90 minutes under vacuum as more gases evolved. The flask was then cooled to room temperature and sealed off at $2 \times 10^{-5}$ Torr. Next, the flask was heated until any Na remaining on the walls of the flask was distilled onto the surface of the silica gel. Finally, the flask was then placed in a furnace at 210° C. overnight. The sample was then distributed into 4 vials. All four vials (812 mg, 771 mg, 823 mg, and 525 mg plus any remainders, respectively) were placed in the freezer.

Example 17—Fragrance Testing

Two samples of Na/silica gel mixture from Example 2 above were obtained from freezer. The first sample weighed 520 mg. 684 mg of Citrus Oil fragrance was freeze pumped 3 times to a pressure of $2 \times 10^{-5}$ Torr and placed in a He filled glove box. The first sample of Na/silica gel mixture was then added to the Citrus Oil in the glove box. The sample was then evacuated with liquid $N_2$ cooling. The sample was then allowed to warm to room temperature and the gases produced by the reaction of the Na/silica gel and the Citrus Oil were measured. The sample was then held at room temperature for 110 minutes to observe reaction. The sample was then cooled with liquid nitrogen and water was allowed to condense onto the sample for 5 minutes. The sample was then allowed to warm to permit reaction of the sample with water. All gases were then collected and measured.

The second sample weighed 109.7 mg. 161 mg of Citrus Oil fragrance was freeze pumped 3 times to a pressure of $2 \times 10^{-5}$ Torr and placed in a He filled glove box. The second sample of Na/silica gel mixture was then added to the Citrus Oil in the glove box. The sample was then evacuated with liquid $N_2$ cooling. The sample was then allowed to warm to room temperature and the gases produced by the reaction of the Na/silica gel and the Citrus Oil were measured. The sample was then held at room temperature for 110 minutes to observe reaction. The sample was then cooled with liquid nitrogen and water was allowed to condense onto the sample for 5 minutes. The sample was then allowed to warm to permit reaction of the sample with water. All gases were then collected and measured.

Example 18—Deodorizer Compositions

A first deodorizer composition containing 0.8 g citric acid, 0.35 g sodium bicarbonate, 0.11 g sodium containing reduced silica gel, and 0.27 g fragrance. A second deodorizer composition containing 0.8 g citric acid, 0.35 g sodium bicarbonate, 0.11 g sodium containing reduced silica gel, and 0.35 g fragrance. A third deodorizer composition containing 0.8 g citric acid, 0.35 g sodium bicarbonate, 0.11 g sodium containing reduced silica gel, and 0.5 g fragrance.

What is claimed is:

1. A Group 1 metal/silica gel composition prepared by a process of:
   mixing a Group 1 metal in liquid form with porous silica gel in an inert atmosphere under isothermal conditions sufficient to absorb the liquid Group 1 metal into the silica gel pores, wherein the Group 1 metal/silica gel composition produced reacts with dry $O_2$.

2. The Group 1 metal/silica gel composition of claim 1 wherein the pores of said silica gel have an average pore size of approximately 50 to 1,000 Å.

3. The Group 1 metal/silica gel composition of claim 1 wherein the pores of said silica gel have an average pore size of approximately 150 Å.

4. The Group 1 metal/silica gel composition of claim 1 wherein the Group 1 metal is selected from the group consisting of rubidium, cesium, and an alloy of two or more Group 1 metals thereof.

5. The Group 1 metal/silica gel composition of claim 4 wherein the Group 1 metal is a sodium-potassium alloy.

6. The Group 1 metal/silica gel composition of claim 1 wherein the Group 1 metal is present in an amount up to 50% by weight load.

7. A Group 1 metal/silica gel composition prepared by a process of:
   mixing a Group 1 metal in liquid form with porous silica gel under exothermic conditions sufficient to absorb the liquid Group 1 metal or liquid Group 1 metal alloy into the silica gel pores, wherein the Group 1 metal/silica gel composition produced does not react with dry $O_2$.

8. The Group 1 metal/silica gel composition of claim 7 wherein the pores of said porous silica gel have an average pore size of approximately 50 to 1,000 Å.

9. The Group 1 metal/silica gel composition of claim 7 wherein the pores of said porous silica gel have an average pore size of approximately 150 Å.

10. The Group 1 metal/silica gel composition of claim 7 wherein the Group 1 metal is selected from the group consisting of rubidium, cesium, an alloy of two or more Group 1 metals thereof.

11. The Group 1 metal/silica gel composition of claim 10 wherein the Group 1 metal is a sodium-potassium alloy.

12. The Group 1 metal/silica gel composition of claim 7 wherein the Group 1 metal is present in an amount up to 50% by weight.

13. A Group 1 metal/silica gel composition prepared by a process of:
   mixing a Group 1 metal in liquid form with porous silica gel under exothermic conditions sufficient to absorb the liquid Group 1 metal into the silica gel pores, and heating the resulting mixture to a temperature of between about 215° C. to about 400° C., wherein the Group 1 metal/silica gel composition produced does not react with dry O$_2$.

14. The Group 1 metal/silica gel composition of claim 13 wherein the pores of said porous silica gel have an average pore size of approximately 50 to 1,000 Å.

15. The Group 1 metal/silica gel composition of claim 13 wherein the pores of said porous silica gel have an average pore size of approximately 150 Å.

16. The Group 1 metal/silica gel composition of claim 13 wherein the Group 1 metal is selected from the group consisting of sodium, potassium, rubidium, cesium, and an alloy of two or more Group 1 metals thereof.

17. The Group 1 metal/silica gel composition of claim 16 wherein the Group 1 metal is sodium, potassium or a sodium-potassium alloy.

18. The Group 1 metal/silica gel composition of claim 13 wherein the Group 1 metal is present in an amount up to about 50% by weight.

19. The Group 1 metal/silica gel composition of claim 18 wherein the loading of the Group 1 metal is present in an amount of 30–40% by weight.

20. A Group 1 metal/silica gel composition prepared by a process of:
mixing a Group 1 metal in liquid form with porous silica gel under exothermic conditions sufficient to absorb the liquid Group 1 metal into the silica gel pores, and
heating the resulting mixture to a temperature of above about 400° C., wherein the Group 1 metal/silica gel composition produced does not react with dry O$_2$.

21. The Group 1 metal/silica gel composition of claim 20 wherein the pores of said porous silica gel have an average pore size of approximately 50 to 1,000 Å.

22. The Group 1 metal/silica gel composition of claim 20 wherein the pores of said porous silica gel have an average pore size of approximately 150 Å.

23. The Group 1 metal/silica gel composition of claim 20 wherein the Group 1 metal is selected from the group consisting of sodium, potassium, rubidium, cesium, and an alloy of two or more Group 1 metals thereof.

24. The Group 1 metal/silica gel composition of claim 23 wherein the Group 1 metal is sodium, potassium, or a sodium-potassium alloy.

25. The Group 1 metal/silica gel composition of claim 20 wherein the Group 1 metal is present in an amount up to 50% by weight.

26. The Group 1 metal/silica gel composition of claim 25 wherein the Group 1 metal is present in an amount of 30–40% by weight.

27. A method of preparing a Stage 0 Group 1 metal/silica gel composition comprising the step of contacting a Group 1 metal in liquid form with porous silica gel under isothermal conditions an inert atmosphere or under a vacuum to absorb the Group 1 metal into the pores of the silica gel.

28. A method of preparing a Stage I Group 1 metal/silica gel composition comprising the step of:
heating the Stage 0 Group 1 metal/silica gel composition of claim 27 to 140° C. for a time and under conditions to convert Stage 0 Group 1 metal/silica gel composition to a Stage I Group 1 metal/silica gel composition.

29. A method of preparing a Stage II Group 1 metal/silica gel composition comprising the step of:
heating the Stage 0 Group 1 metal/silica gel composition of claim 27 to a temperature of between about 215° C. to about 400° C. for a time and under conditions to convert Stage 0 Group 1 metal/silica gel composition to a Stage II Group 1 metal/silica gel composition.

30. A method of preparing a Stage III Group 1 metal/silica gel composition comprising the step of:
heating the Stage 0 Group 1 metal/silica gel composition of claim 27 to a temperature above about 500° C. for a time and under conditions to convert Stage 0 Group 1 metal/silica gel composition to a Stage III Group 1 metal/silica gel composition.

31. A method of preparing a Stage I Group 1 metal/silica gel composition comprising the step of:
mixing a Group 1 metal in liquid form with porous silica gel under exothermic conditions sufficient to absorb the liquid Group 1 metal into the silica gel pores.

32. A method of preparing a Stage II Group 1 metal/silica gel composition comprising the steps of:
mixing a Group 1 metal in liquid form with porous silica gel under exothermic conditions sufficient to absorb the liquid Group 1 metal into the silica gel pores, and
heating the resulting mixture to a temperature of between about 215° C. to about 400° C.

33. A method of preparing a Stage III Group 1 metal/silica gel composition comprising the steps of:
mixing a Group 1 metal in liquid form with porous silica gel under exothermic conditions sufficient to absorb the liquid Group 1 metal into the silica gel pores, and
heating the resulting mixture to a temperature above about 500° C.

* * * * *